(12) United States Patent
Amamoto et al.

(10) Patent No.: US 12,241,860 B2
(45) Date of Patent: Mar. 4, 2025

(54) SENSOR AND MANUFACTURING METHOD THEREOF

(71) Applicant: ROHM Co., LTD., Kyoto (JP)

(72) Inventors: Yurina Amamoto, Kyoto (JP); Shunsuke Akasaka, Kyoto (JP)

(73) Assignee: ROHM Co., LTD., Kyoto (JP)

( * ) Notice: Subject to any disclaimer, the term of this patent is extended or adjusted under 35 U.S.C. 154(b) by 164 days.

(21) Appl. No.: 17/499,991

(22) Filed: Oct. 13, 2021

(65) Prior Publication Data

US 2022/0120708 A1 Apr. 21, 2022

(30) Foreign Application Priority Data

Oct. 15, 2020 (JP) .................. 2020-173784

(51) Int. Cl.
*G01N 27/416* (2006.01)
*C23F 1/02* (2006.01)
(Continued)

(52) U.S. Cl.
CPC ........... *G01N 27/4163* (2013.01); *C23F 1/02* (2013.01); *C23F 1/12* (2013.01); *G01N 1/44* (2013.01);
(Continued)

(58) Field of Classification Search
CPC ............. G01N 27/4163; G01N 27/407; G01N 27/4071; G01N 1/44; G01N 33/0027; C23F 1/02; C23F 1/12
See application file for complete search history.

(56) References Cited

U.S. PATENT DOCUMENTS

2002/0070195 A1* 6/2002 Wado .................... G01L 9/0042
216/75
2006/0154401 A1* 7/2006 Gardner ............... G01N 27/128
438/53
(Continued)

FOREIGN PATENT DOCUMENTS

CN 109809356 A * 5/2019
JP 2002-181603 6/2002
(Continued)

OTHER PUBLICATIONS

Ahn et al., English translation of KR101686123B1, 2016 (Year: 2016).*
(Continued)

*Primary Examiner* — Luan V Van
*Assistant Examiner* — Shizhi Qian
(74) *Attorney, Agent, or Firm* — CHIP LAW GROUP

(57) ABSTRACT

Provided is a sensor including a substrate that includes a major surface, a sensor part that includes a gas flow path formed of a porous material, and at least one of a heater or a temperature sensor. The heater is capable of heating the sensor part, the temperature sensor is capable of measuring temperature of the sensor part, the sensor part and the at least one of the heater or the temperature sensor are stacked over the major surface, the at least one of the heater or the temperature sensor is an interconnect having forward tapered side surfaces, and the at least one of the heater or the temperature sensor includes a metal interconnect layer, and the forward tapered side surfaces of the interconnect overlap with the gas flow path in plan view of the major surface.

14 Claims, 24 Drawing Sheets

(51) Int. Cl.
  *C23F 1/12*      (2006.01)
  *G01N 1/44*     (2006.01)
  *G01N 27/407*  (2006.01)
  *G01N 33/00*   (2006.01)
(52) U.S. Cl.
  CPC ....... *G01N 27/407* (2013.01); *G01N 33/0027* (2013.01)

(56) References Cited

U.S. PATENT DOCUMENTS

| | | | |
|---|---|---|---|
| 2014/0296095 A1* | 10/2014 | Lin | G01N 33/569 435/6.14 |
| 2017/0122898 A1* | 5/2017 | Akasaka | G01N 27/304 |
| 2017/0167999 A1* | 6/2017 | Akasaka | B81B 7/0061 |
| 2017/0299543 A1* | 10/2017 | Akasaka | G01N 27/407 |
| 2018/0031506 A1* | 2/2018 | Shankar | G01N 27/129 |
| 2018/0106745 A1* | 4/2018 | Shibasaki | G01N 27/16 |
| 2020/0209185 A1* | 7/2020 | Watanabe | G01N 27/4077 |
| 2020/0256270 A1* | 8/2020 | Takeuchi | G01N 27/4065 |

FOREIGN PATENT DOCUMENTS

| | | | |
|---|---|---|---|
| JP | 2006072169 | | 3/2006 |
| JP | 2013003068 A | * | 1/2013 |
| JP | 2015-212649 | | 11/2015 |
| KR | 101686123 B1 | * | 12/2016 |

OTHER PUBLICATIONS

Chu et al., English translation of CN-109809356-A, 2019 (Year: 2019).*
Ryosuke et al., English translation of JP-2013003068-A, 2013 (Year: 2013).*
Chang et al., Multilayer microheater based on glass substrate using MEMS technology, Microelectronic Engineering, 2016, 149, 25-30 (Year: 2016).*
Notice of Reasons for Refusal cited in Japanese Application No. 2020173784, mailed on Apr. 9, 2024.

* cited by examiner

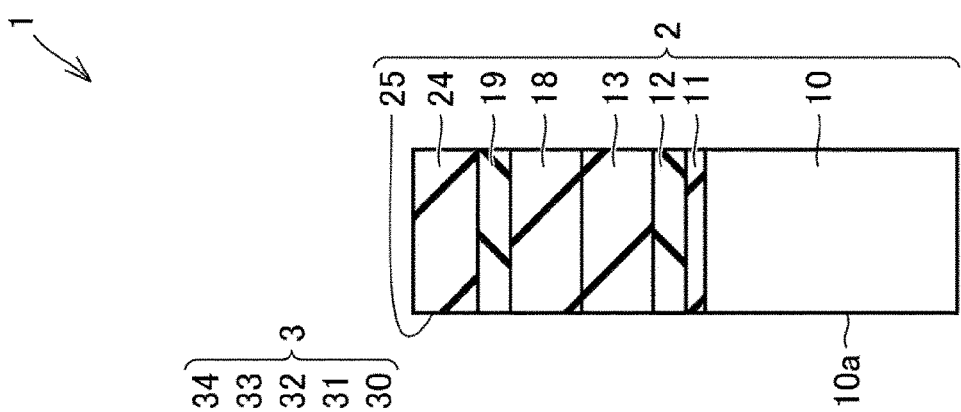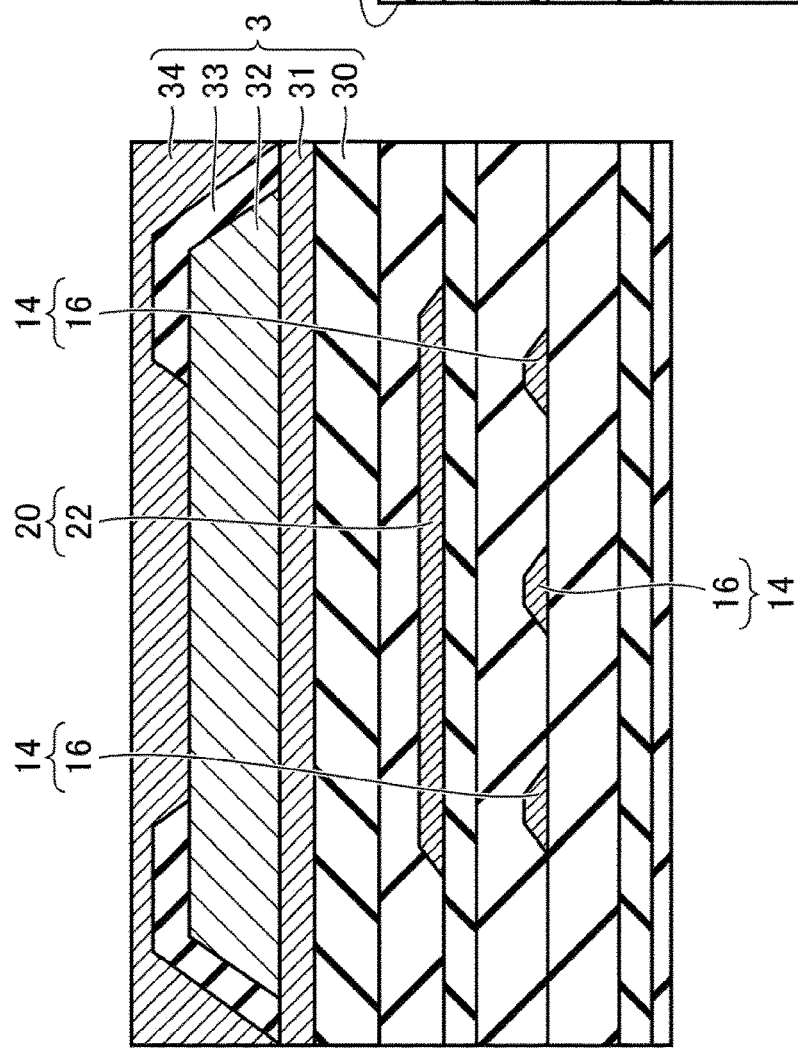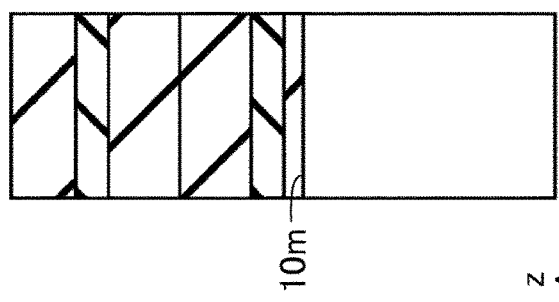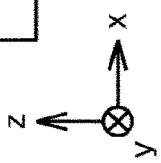
FIG. 31

SENSOR AND MANUFACTURING METHOD THEREOF

CROSS REFERENCE TO RELATED APPLICATIONS

This application claims priority benefit of Japanese Patent Application No. JP 2020-173784 filed in the Japan Patent Office on Oct. 15, 2020. Each of the above-referenced applications is hereby incorporated herein by reference in its entirety.

BACKGROUND

The present disclosure relates to a sensor and a manufacturing method thereof.

Japanese Patent Laid-open No. 2004-257963 discloses a limiting current-type gas sensor including a solid electrolyte layer, a cathode, an anode, a gas introduction path that introduces a measurement gas to the cathode, and a gas discharge path that discharges a discharged gas from the anode.

SUMMARY

It is desirable to provide a sensor in which variation in characteristics is reduced and a manufacturing method thereof.

According to an embodiment of the present disclosure, there is provided a sensor including a substrate that includes a major surface, a sensor part that includes a gas flow path formed of a porous material, and at least one of a heater or a temperature sensor. The heater is capable of heating the sensor part. The temperature sensor is capable of measuring temperature of the sensor part. The sensor part and the at least one of the heater or the temperature sensor are stacked over the major surface of the substrate. The at least one of the heater or the temperature sensor is an interconnect having forward tapered side surfaces. The at least one of the heater or the temperature sensor includes a metal interconnect layer. The forward tapered side surfaces of the interconnect overlap with the gas flow path in plan view of the major surface of the substrate.

According to an embodiment of the present disclosure, there is provided a manufacturing method of a sensor including forming at least one of a heater or a temperature sensor and forming a sensor part including a gas flow path formed of a porous material. The heater is capable of heating the sensor part. The temperature sensor is capable of measuring temperature of the sensor part. The sensor part and the at least one of the heater or the temperature sensor are stacked over a major surface of a substrate. The at least one of the heater or the temperature sensor is an interconnect having forward tapered side surfaces. The forming the at least one of the heater or the temperature sensor includes forming a metal interconnect layer. The forward tapered side surfaces of the interconnect overlap with the gas flow path in plan view of the major surface of the substrate.

According to the sensor of the embodiment of the present disclosure, variation in characteristics of the sensor can be reduced. According to the manufacturing method of a sensor of the embodiment of the present disclosure, the sensor in which variation in characteristics is reduced can be obtained.

BRIEF DESCRIPTION OF THE DRAWINGS

FIG. 31 is a schematic sectional view of a second modification example of the embodiment.

DETAILED DESCRIPTION OF THE PREFERRED EMBODIMENTS

An embodiment will be described below. The same configuration is given the same reference sign, and description thereof is not repeated.

Embodiment

A sensor 1 of the embodiment will be described with reference to FIG. 1 to FIG. 4. The sensor 1 is a gas sensor, for example.

Figure 1:
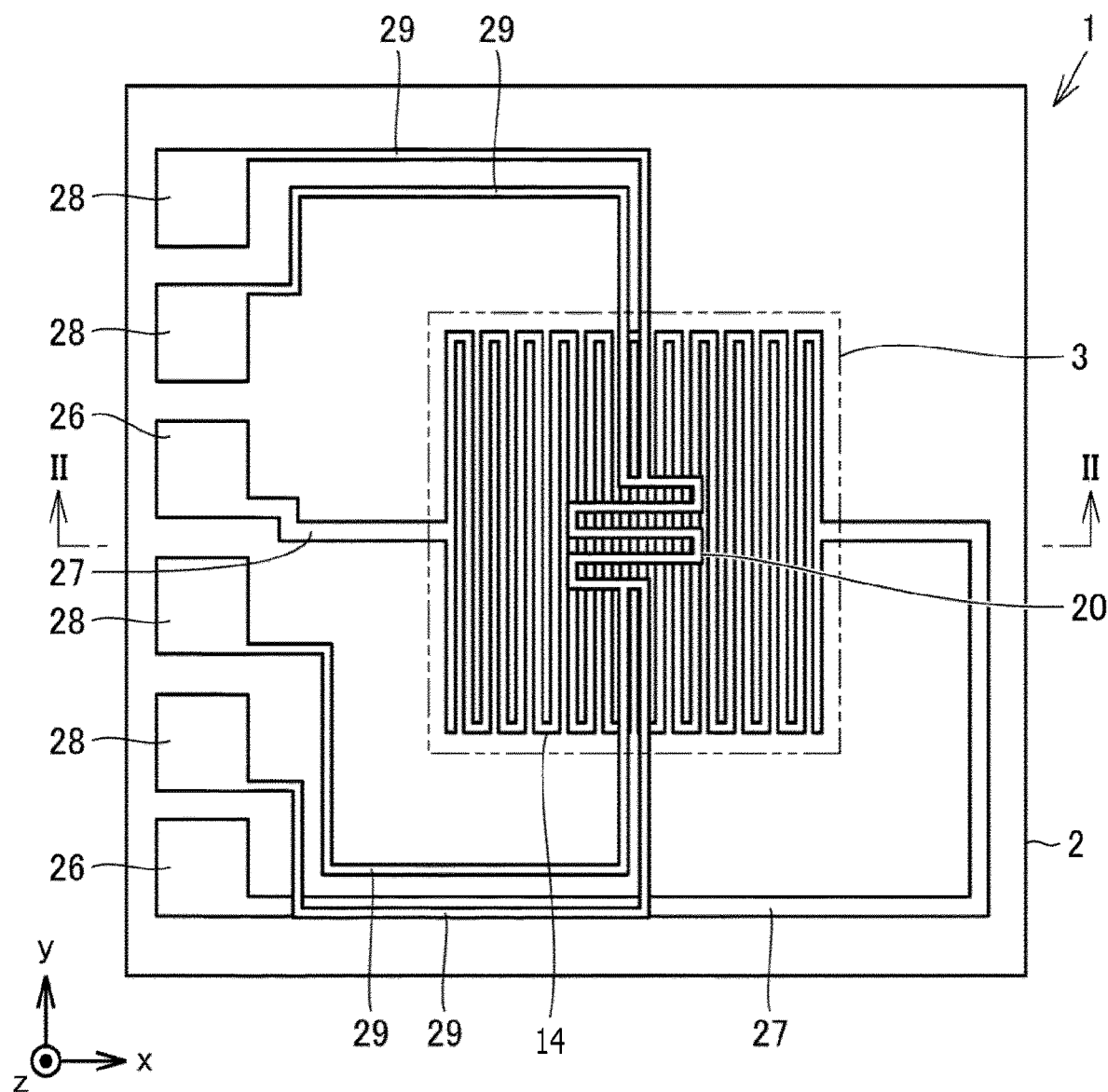
FIG. 1 is a schematic plan view of a sensor of an embodiment of the present disclosure.
Figure 2:
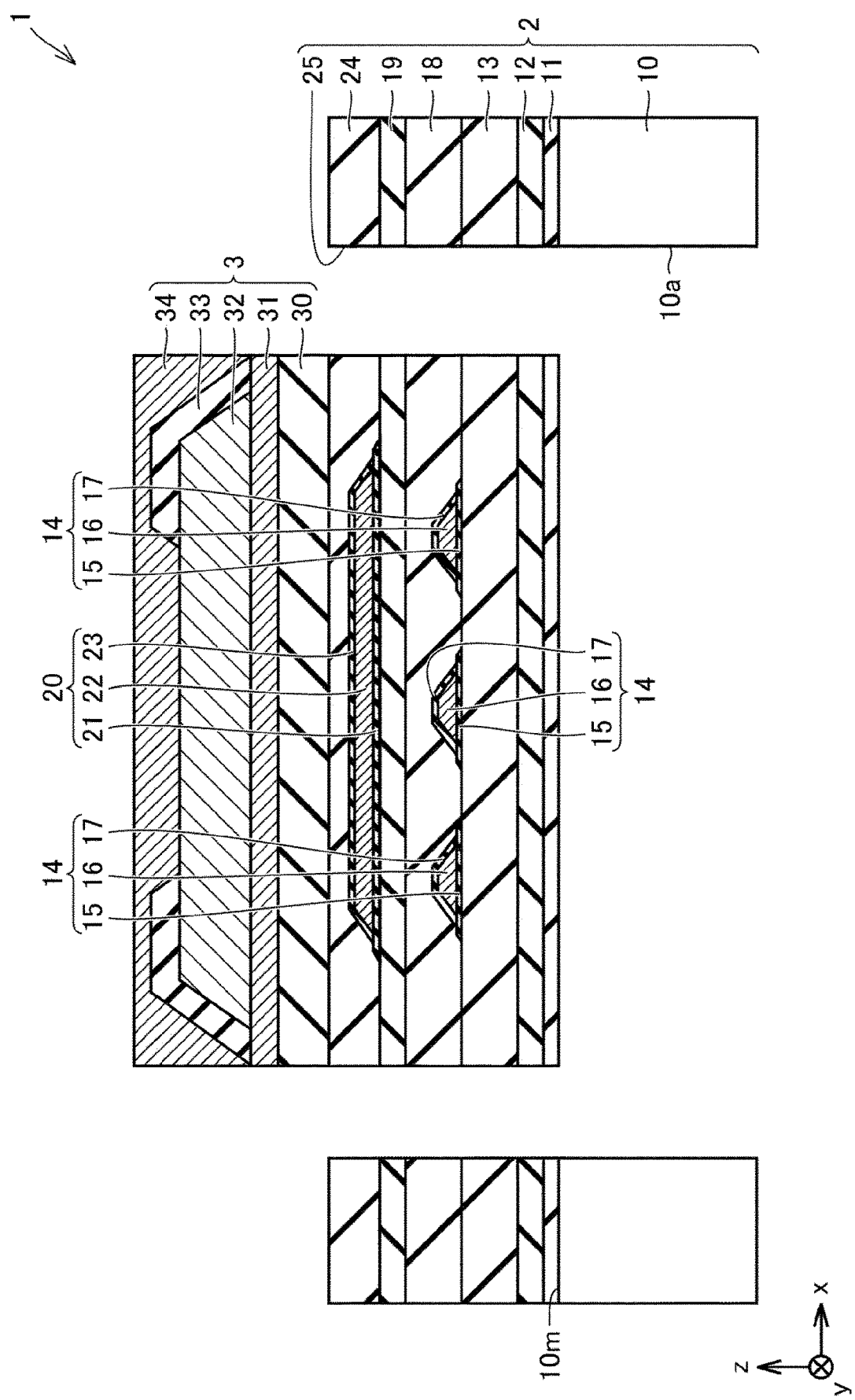
FIG. 2 is a schematic sectional view of the sensor of the embodiment along section line II-II illustrated in FIG. 1.

Referring to FIG. 1 and FIG. 2, the sensor 1 mainly includes a substrate 10, a heater 14, a temperature sensor 20, and a sensor part 3. The sensor part 3, the heater 14, and the temperature sensor 20 are stacked over a major surface 10m of the substrate 10. The sensor 1 further includes insulating layers 11, 13, 18, and 24 and nitride layers 12 and 19.

The substrate 10 is a silicon substrate but is not particularly limited. The substrate 10 includes the major surface 10m. An opening 10a is made in the substrate 10. The opening 10a of the substrate 10 extends to the major surface 10m of the substrate 10 and decreases the contact area between the substrate 10 and the insulating layer 11. Thus, it becomes hard for heat generated from the heater 14 to be dissipated to the substrate 10, and the power consumption of the heater 14 can be reduced. Due to the opening 10a of the substrate 10, the sensor part 3 is formed into a beam structure with both ends supported by the substrate 10. Thus, the heat capacity of the sensor part 3 is reduced, and the sensitivity of the sensor part 3 can be improved.

The insulating layer 11 is disposed on the major surface 10m of the substrate 10. The insulating layer 11 is formed of silicon dioxide, for example. The nitride layer 12 is disposed on the insulating layer 11. The nitride layer 12 is formed of silicon nitride, for example. The insulating layer 13 is disposed on the nitride layer 12. The insulating layer 13 is formed of silicon dioxide, for example. The insulating layers 11 and 13 and the nitride layer 12 electrically insulate the heater 14 from the substrate 10.

Figure 3:
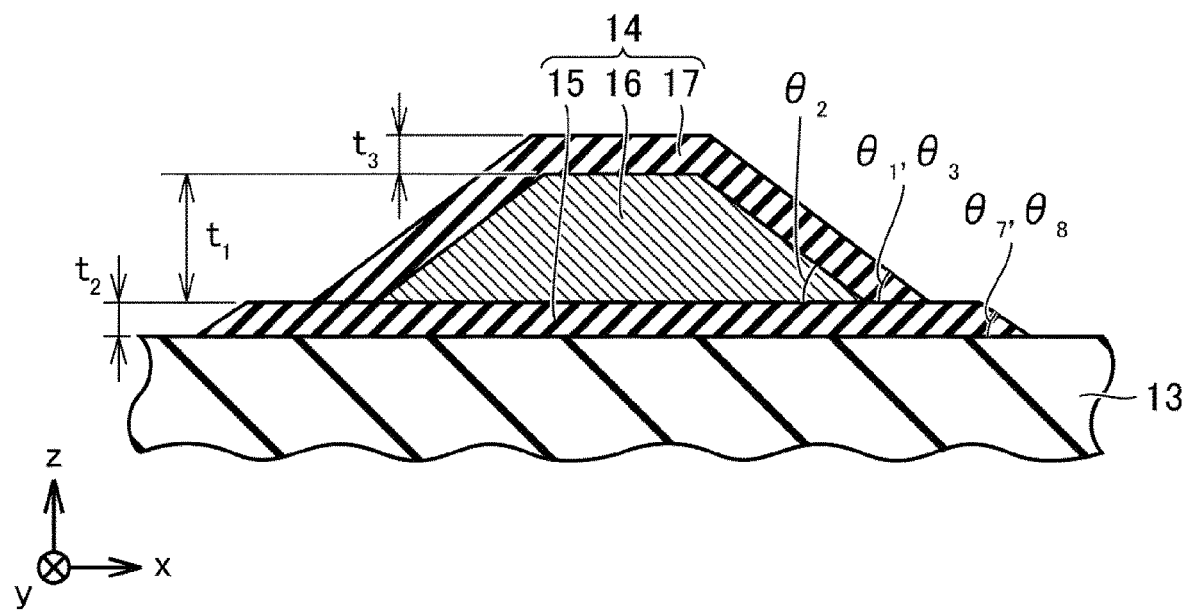
FIG. 3 is a schematic partially-enlarged sectional view of a heater included in the sensor of the embodiment.

Referring to FIG. 2 and FIG. 3, the heater 14 is formed on the insulating layer 13. The heater 14 can heat the sensor part 3. For example, the heater 14 heats a solid electrolyte layer 32 in order to enable ion conduction in the solid electrolyte layer 32. The heater 14 is disposed over the major surface 10m of the substrate 10. Referring to FIG. 1, in plan view of the major surface 10m of the substrate 10, the heater 14 may meander and may be a meandering heater interconnect. In plan view of the major surface 10m of the substrate 10, the heater 14 is surrounded by the edge of the opening 10a of the substrate 10. Thus, it becomes hard for heat generated by the heater 14 to be dissipated to the substrate 10, and the heat can be efficiently applied to the sensor part 3.

The heater 14 is a heater interconnect having forward tapered side surfaces. In the present specification, the forward tapered side surfaces of an interconnect or the like mean the side surfaces of the interconnect or the like that cause the sectional shape of the interconnect or the like in a section perpendicular to the longitudinal direction of the interconnect or the like to be a shape tapered as the position gets further away from the surface on which the interconnect or the like is formed. In plan view of the major surface 10m of the substrate 10, the forward tapered side surfaces of the heater interconnect overlap with a gas flow path 30.

Taper angles $\theta_1$ and $\theta_7$ of the forward tapered side surfaces of the heater interconnect are each equal to or smaller than 45°, for example. In the present specification, the taper angle of the forward tapered side surface of an interconnect or the like means the angle between the surface on which the interconnect or the like is formed and the forward tapered side surface of the interconnect or the like. The taper angles $\theta_1$ and $\theta_7$ of the forward tapered side surfaces of the heater interconnect may be each equal to or smaller than 40°, and may be each equal to or smaller than 35°, and may be each equal to or smaller than 30°, and may be each equal to or smaller than 25°, and may be each equal to or smaller than 20°, and may be each equal to or smaller than 15°, and may be each equal to or smaller than 10°. The taper angles $\theta_1$ and $\theta_7$ of the forward tapered side surfaces of the heater interconnect are each larger than 0°. In the present embodiment, the taper angle $\theta_1$ of the forward tapered side surfaces of the heater interconnect is given by a taper angle $\theta_3$ of the forward tapered outer side surfaces of a close contact layer 17 to be described later. The taper angle $\theta_7$ of the forward tapered side surfaces of the heater interconnect is given by a taper angle $\theta_8$ of the forward tapered outer side surfaces of a close contact layer 15 to be described later.

The heater 14 includes a metal interconnect layer 16. The metal interconnect layer 16 is formed of platinum, for example. A thickness $t_1$ of the metal interconnect layer 16 is at least 100 nm and at most 200 nm, for example. The metal interconnect layer 16 has forward tapered side surfaces. A taper angle $\theta_2$ of the forward tapered side surfaces of the metal interconnect layer 16 is equal to or smaller than 45°, for example. The taper angle $\theta_2$ of the forward tapered side surfaces of the metal interconnect layer 16 may be equal to or smaller than 40°, and may be equal to or smaller than 35°, and may be equal to or smaller than 30°, and may be equal to or smaller than 25°, and may be equal to or smaller than 20°, and may be equal to or smaller than 15°, and may be equal to or smaller than 10°. The taper angle $\theta_2$ of the forward tapered side surfaces of the metal interconnect layer 16 is larger than 0°. In plan view of the major surface 10m of the substrate 10, the forward tapered side surfaces of the metal interconnect layer 16 overlap with the gas flow path 30.

The heater 14 further includes the close contact layers 15 and 17 that cover the metal interconnect layer 16. The metal interconnect layer 16 is covered by the close contact layers 15 and 17 in the section perpendicular to the longitudinal direction of the heater 14 (metal interconnect layer 16). The close contact layers 15 and 17 are formed of a transition metal oxide such as titanium oxide, chromium oxide, tungsten oxide, molybdenum oxide, or tantalum oxide, for example. The close contact layer 15 is disposed between the insulating layer 13 and the metal interconnect layer 16. The close contact layer 15 improves close contact between the metal interconnect layer 16 and the insulating layer 13. The close contact layer 15 is in contact with the insulating layer 18 and is in close contact with the insulating layer 18. The close contact layer 17 is disposed between the insulating layer 18 and the metal interconnect layer 16. The close contact layer 17 improves close contact between the metal interconnect layer 16 and the insulating layer 18. The thickness of each of the close contact layers 15 and 17 is smaller than the thickness of the metal interconnect layer 16. A thickness $t_2$ of the close contact layer 15 and a thickness $t_3$ of the close contact layer 17 are each at least 20 nm and at most 30 nm, for example.

The close contact layer 15 has forward tapered outer side surfaces in contact with the insulating layer 18. The taper angle $\theta_8$ of the outer side surfaces of the close contact layer 15 is equal to or smaller than 45°, for example. The taper angle $\theta_8$ of the outer side surfaces of the close contact layer 15 may be equal to or smaller than 40°, and may be equal to or smaller than 35°, and may be equal to or smaller than 30°, and may be equal to or smaller than 25°, and may be equal to or smaller than 20°, and may be equal to or smaller than 15°, and may be equal to or smaller than 10°. The taper angle $\theta_8$ of the outer side surfaces of the close contact layer 15 is larger than 0°. In plan view of the major surface 10$m$ of the substrate 10, the outer side surfaces of the close contact layer 15 overlap with the gas flow path 30.

The close contact layer 17 has forward tapered outer side surfaces in contact with the insulating layer 18. The taper angle $\theta_3$ of the outer side surfaces of the close contact layer 17 is equal to or smaller than 45°, for example. The taper angle $\theta_3$ of the outer side surfaces of the close contact layer 17 may be equal to or smaller than 40°, and may be equal to or smaller than 35°, and may be equal to or smaller than 30°, and may be equal to or smaller than 25°, and may be equal to or smaller than 20°, and may be equal to or smaller than 15°, and may be equal to or smaller than 10°. The taper angle $\theta_3$ of the outer side surfaces of the close contact layer 17 is larger than 0°. In plan view of the major surface 10$m$ of the substrate 10, the outer side surfaces of the close contact layer 17 overlap with the gas flow path 30.

Referring to FIG. 2, the insulating layer 18 is disposed on the insulating layer 13 and the heater 14. The heater 14 is filled in the insulating layer 18. The insulating layer 18 is formed of silicon dioxide, for example. The nitride layer 19 is disposed on the insulating layer 18. The nitride layer 19 is formed of silicon nitride, for example.

Figure 4:
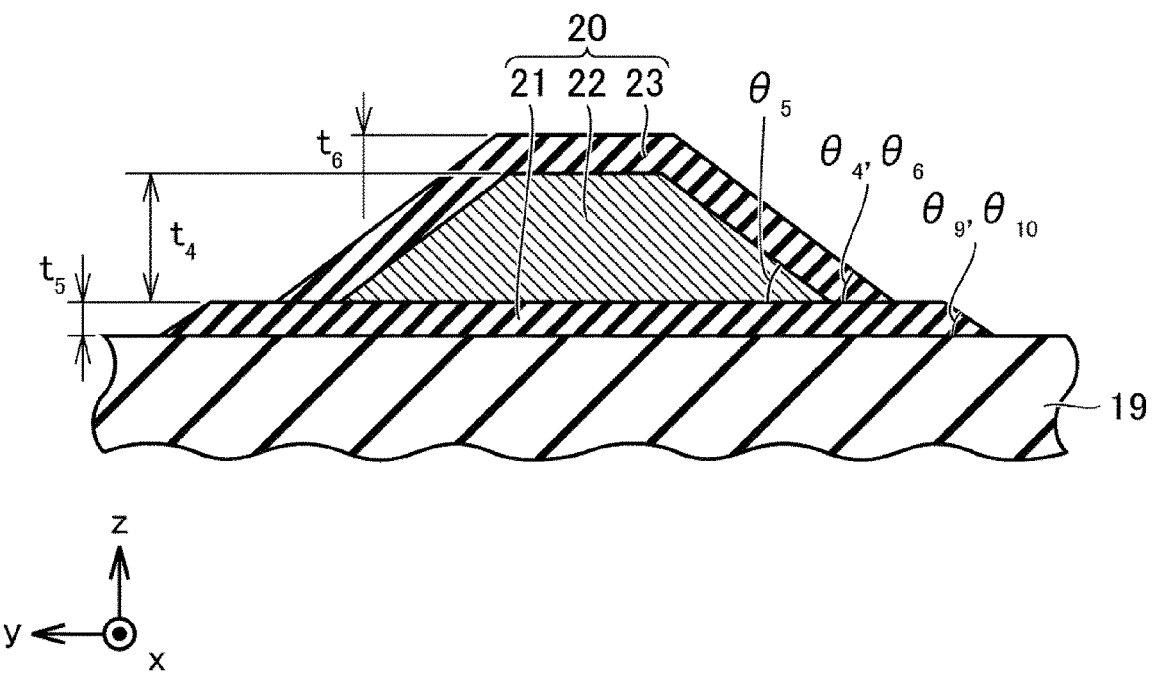
FIG. 4 is a schematic partially-enlarged sectional view of a temperature sensor included in the sensor of the embodiment.

Referring to FIG. 2 and FIG. 4, the temperature sensor 20 is formed on the nitride layer 19. The temperature sensor 20 can measure the temperature of the sensor part 3. The temperature sensor 20 is a temperature sensor interconnect having forward tapered side surfaces. In plan view of the major surface 10$m$ of the substrate 10, the forward tapered side surfaces of the temperature sensor interconnect overlap with the gas flow path 30.

Taper angles $\theta_4$ and $\theta_9$ of the forward tapered side surfaces of the temperature sensor interconnect are each equal to or smaller than 45°, for example. The taper angles $\theta_4$ and $\theta_9$ of the forward tapered side surfaces of the temperature sensor interconnect may be each equal to or smaller than 40°, and may be each equal to or smaller than 35°, and may be each equal to or smaller than 30°, and may be each equal to or smaller than 25°, and may be each equal to or smaller than 20°, and may be each equal to or smaller than 15°, and may be each equal to or smaller than 10°. The taper angles $\theta_4$ and $\theta_9$ of the forward tapered side surfaces of the temperature sensor interconnect are each larger than 0°. In the present embodiment, the taper angle $\theta_4$ of the forward tapered side surfaces of the temperature sensor interconnect is given by a taper angle $\theta_6$ of the forward tapered outer side surfaces of a close contact layer 23 to be described later. The taper angle $\theta_9$ of the forward tapered side surfaces of the temperature sensor interconnect is given by a taper angle $\theta_{10}$ of the forward tapered outer side surfaces of a close contact layer 21 to be described later.

The temperature sensor 20 includes a metal interconnect layer 22. The metal interconnect layer 22 is formed of platinum, for example. A thickness $t_4$ of the metal interconnect layer 22 is at least 100 nm and at most 200 nm, for example. The metal interconnect layer 22 has forward tapered side surfaces. A taper angle $\theta_5$ of the forward tapered side surfaces of the metal interconnect layer 22 is equal to or smaller than 45°, for example. The taper angle $\theta_5$ of the forward tapered side surfaces of the metal interconnect layer 22 may be equal to or smaller than 40°, and may be equal to or smaller than 35°, and may be equal to or smaller than 30°, and may be equal to or smaller than 25°, and may be equal to or smaller than 20°, and may be equal to or smaller than 15°, and may be equal to or smaller than 10°. The taper angle $\theta_5$ of the forward tapered side surfaces of the metal interconnect layer 22 is larger than 0°. In plan view of the major surface 10$m$ of the substrate 10, the forward tapered side surfaces of the metal interconnect layer 22 overlap with the gas flow path 30.

The temperature sensor 20 further includes the close contact layers 21 and 23 that cover the metal interconnect layer 22. The metal interconnect layer 22 is covered by the close contact layers 21 and 23 in the section perpendicular to the longitudinal direction of the temperature sensor 20 (metal interconnect layer 22). The close contact layers 21 and 23 are formed of a transition metal oxide such as titanium oxide, chromium oxide, tungsten oxide, molybdenum oxide, or tantalum oxide, for example. The close contact layer 21 is disposed between the nitride layer 19 and the metal interconnect layer 22. The close contact layer 21 improves close contact between the metal interconnect layer 22 and the nitride layer 19. The close contact layer 21 is in contact with the insulating layer 24 and is in close contact with the insulating layer 24. The close contact layer 23 is disposed between the insulating layer 24 and the metal interconnect layer 22. The close contact layer 23 improves close contact between the metal interconnect layer 22 and the insulating layer 24. The thickness of each of the close contact layers 21 and 23 is smaller than the thickness of the metal interconnect layer 22. A thickness $t_6$ of the close contact layer 21 and a thickness $t_6$ of the close contact layer 23 are each at least 20 nm and at most 30 nm, for example.

The close contact layer 21 has forward tapered outer side surfaces in contact with the insulating layer 24. The taper angle $\theta_{10}$ of the outer side surfaces of the close contact layer 21 is equal to or smaller than 45°, for example. The taper angle $\theta_{10}$ of the outer side surfaces of the close contact layer 21 may be equal to or smaller than 40°, and may be equal to or smaller than 35°, and may be equal to or smaller than 30°, and may be equal to or smaller than 25°, and may be equal to or smaller than 20°, and may be equal to or smaller than 15°, and may be equal to or smaller than 10°. The taper angle $\theta_{10}$ of the outer side surfaces of the close contact layer 21 is larger than 0°. In plan view of the major surface 10$m$ of the substrate 10, the outer side surfaces of the close contact layer 21 overlap with the gas flow path 30.

The close contact layer 23 has forward tapered outer side surfaces in contact with the insulating layer 24. The taper angle $\theta_6$ of the outer side surfaces of the close contact layer 23 is equal to or smaller than 45°, for example. The taper angle $\theta_6$ of the outer side surfaces of the close contact layer 23 may be equal to or smaller than 40°, and may be equal to or smaller than 35°, and may be equal to or smaller than 30°, and may be equal to or smaller than 25°, and may be equal to or smaller than 20°, and may be equal to or smaller than 15°, and may be equal to or smaller than 10°. The taper angle $\theta_6$ of the outer side surfaces of the close contact layer 23 is larger than 0°. In plan view of the major surface 10$m$ of the substrate 10, the outer side surfaces of the close contact layer 23 overlap with the gas flow path 30.

Referring to FIG. 2, the insulating layer 24 is disposed on the nitride layer 19 and the temperature sensor 20. The temperature sensor 20 is filled in the insulating layer 24. The insulating layer 24 protects the temperature sensor 20. The insulating layer 24 is formed of silicon nitride, for example.

The sensor part 3 is disposed on a multilayer structure including the insulating layers 11, 13, 18, and 24 and the nitride layers 12 and 19, i.e., a multilayer structure including silicon dioxide layers and silicon nitride layers. The thermal expansion coefficient of this multilayer structure is closer to the thermal expansion coefficient of the metal interconnect layer 16 of the heater 14 (for example, thermal expansion coefficient of platinum) than the thermal expansion coefficient of silicon dioxide. Thus, thermal stress applied to the sensor part 3 while the sensor part 3 is heated by the heater 14 in order to cause the sensor part 3 to operate can be decreased. In the multilayer structure including the insulating layers 11, 13, 18, and 24 and the nitride layers 12 and 19, an opening 25 that communicates with the opening 10$a$ of the substrate 10 is made.

In the present embodiment, the sensor 1 is a limiting current-type gas sensor. For example, the limiting current-type gas sensor can measure the concentration of nitrogen oxides ($NO_X$) contained in a gas such as the exhaust gas of an automobile. For example, the limiting current-type gas sensor can measure the concentration of oxygen ($O_2$) contained in a gas or the concentration of water vapor ($H_2O$) contained in a gas. The sensor part 3 includes the gas flow path 30, a first porous electrode 31, the solid electrolyte layer 32, and a second porous electrode 34. The sensor part 3 may further include an insulating layer 33.

The gas flow path 30 is disposed on the insulating layer 24. The gas flow path 30 extends from an inlet (not illustrated) of the gas to a part facing the solid electrolyte layer 32 in the first porous electrode 31. The gas flow path 30 is formed of a porous material. The gas flow path 30 limits the amount of flow of the gas to the solid electrolyte layer 32 per unit time. The film density of the gas flow path 30 is equal to or lower than 80% for example. Thus, it becomes easy for the gas to pass through the gas flow path 30 and the response time of the sensor 1 can be shortened. Furthermore, thermal strain generated in the sensor 1 at the time of operation of the sensor 1 can be alleviated by the gas flow path 30. The film density of the gas flow path 30 may be equal to or lower than 60% and may be equal to lower than 45% for example.

The gas flow path 30 may have a higher melting point than the first porous electrode 31 and the second porous electrode 34. The gas flow path 30 may be formed of a porous transition metal oxide having a higher melting point than the metal that forms the first porous electrode 31 and the second porous electrode 34. In the present specification, the transition metals mean the elements of Group 3 to Group 11 in the long periodic table of elements by International Union of Pure and Applied Chemistry (IUPAC). The porous transition metal oxide is tantalum pentoxide ($Ta_2O_5$), titanium dioxide ($TiO_2$), or chromium oxide (III) ($Cr_2O_3$), for example.

The first porous electrode 31 is formed over the gas flow path 30. The first porous electrode 31 may be in contact with the gas flow path 30. The first porous electrode 31 readily causes the gas to pass therethrough from the gas flow path 30 to the solid electrolyte layer 32. The first porous electrode 31 is formed of platinum (Pt) or palladium (Pd), for example. In plan view of the major surface 10$m$ of the substrate 10, the forward tapered side surfaces of the heater interconnect and the forward tapered side surfaces of the temperature sensor interconnect overlap with the first porous electrode 31.

The solid electrolyte layer 32 is disposed on the first porous electrode 31. The solid electrolyte layer 32 is in contact with the first porous electrode 31. The solid electrolyte layer 32 is an ion conductor such as an oxygen ion conductor. For example, the solid electrolyte layer 32 is an oxygen ion conductor in which CaO, MgO, $Y_2O_3$, $Yb_2O_3$, or other substances is added as a stabilizer to a base material such as $ZrO_2$, $HfO_2$, $ThO_2$, or $Bi_2O_3$. Specifically, the solid electrolyte layer 32 is formed of yttria-stabilized zirconia (YSZ). The solid electrolyte layer 32 may be an oxygen ion conductor formed of (La, Sr, Ga, Mg, Co)$O_3$, for example. The solid electrolyte layer 32 has ion conductivity by being heated by the heater 14. At the time of operation of the sensor 1, the solid electrolyte layer 32 is heated at a temperature that is at least 400° C. and at most 750° C., for example, by using the heater 14. In plan view of the major surface 10$m$ of the substrate 10, the forward tapered side surfaces of the heater interconnect and the forward tapered side surfaces of the temperature sensor interconnect overlap with the solid electrolyte layer 32.

The insulating layer 33 is disposed between the first porous electrode 31 and the second porous electrode 34. The insulating layer 33 electrically insulates the second porous electrode 34 from the first porous electrode 31. The insulating layer 33 may be further disposed on part of the solid electrolyte layer 32. The surface of part of the solid electrolyte layer 32 is exposed from the insulating layer 33. The insulating layer 33 is formed of silicon dioxide, for example.

The second porous electrode 34 is formed on the solid electrolyte layer 32 and on the insulating layer 33. The second porous electrode 34 is in contact with the surface of the solid electrolyte layer 32 exposed from the insulating layer 33. The second porous electrode 34 readily causes the gas discharged from the solid electrolyte layer 32 to pass therethrough. The second porous electrode 34 is formed of platinum (Pt) or palladium (Pd), for example. In plan view of the major surface 10$m$ of the substrate 10, the forward tapered side surfaces of the heater interconnect and the forward tapered side surfaces of the temperature sensor interconnect overlap with the second porous electrode 34.

Referring to FIG. 1, the sensor 1 may further include electrically-conductive pads 26 and 28 and electrical interconnects 27 and 29. The metal interconnect layer 16 of the heater 14 is electrically connected to the electrically-conductive pads 26 through the electrical interconnects 27. The metal interconnect layer 22 of the temperature sensor 20 is electrically connected to the electrically-conductive pads 28 through the electrical interconnects 29. The electrically-conductive pads 26 and 28 and the electrical interconnects 27 and 29 are formed of an electrically-conductive material such as platinum, for example. In plan view of the major surface 10$m$ of the substrate 10, the electrically-conductive pads 26 and 28 are exposed from the sensor part 3.

One example of a manufacturing method of the sensor 1 of the present embodiment will be described with reference to FIG. 1 to FIG. 28.

Figure 5:
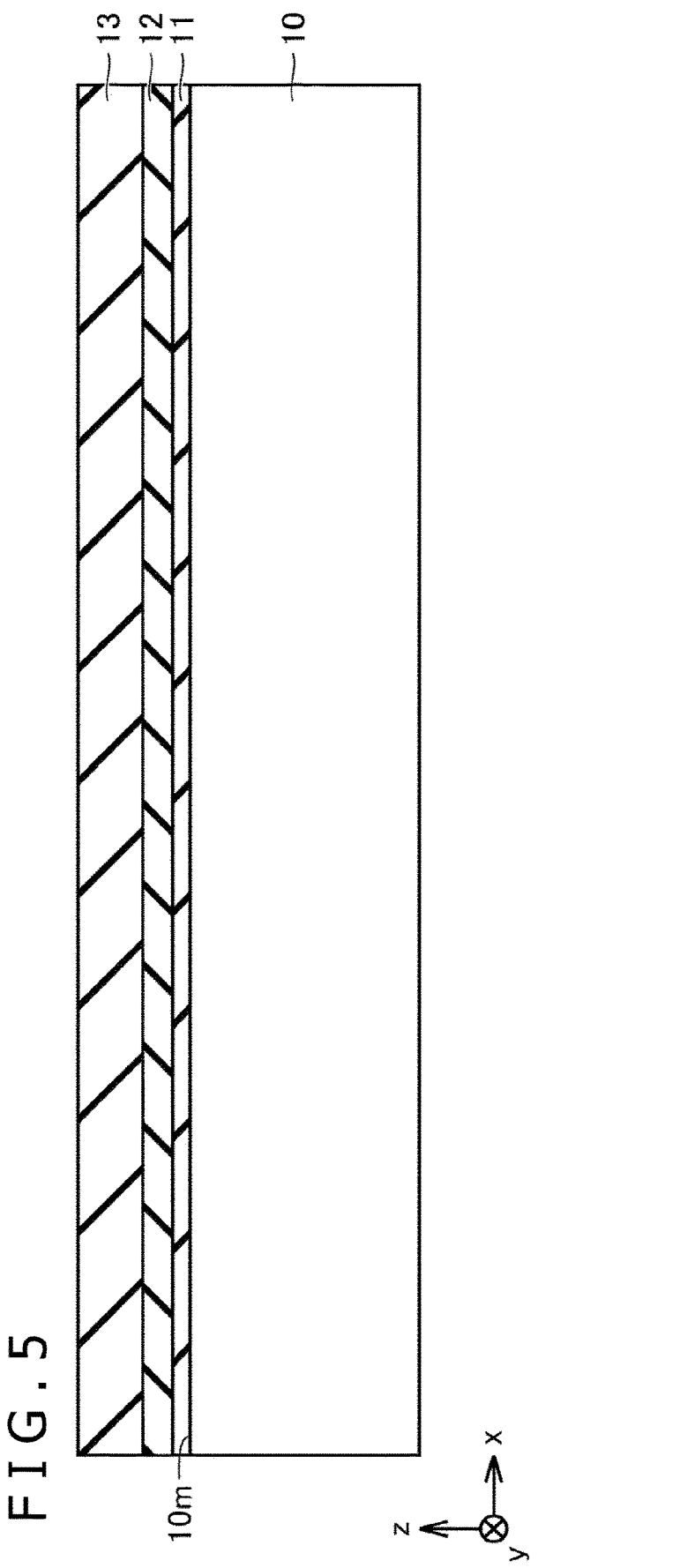
FIG. 5 is a schematic sectional view illustrating one step of a manufacturing method of the sensor of the embodiment.

Referring to FIG. 5, the insulating layer 11 is formed on the major surface 10*m* of the substrate 10 by a chemical vapor deposition (CVD) method. The substrate 10 is a silicon substrate, for example. The insulating layer 11 is formed of silicon dioxide, for example. The nitride layer 12 is formed on the insulating layer 11 by a CVD method. The nitride layer 12 is formed of silicon nitride, for example. The insulating layer 13 is formed on the nitride layer 12 by a CVD method. The insulating layer 13 is formed of silicon dioxide, for example.

Referring to FIG. 6 to FIG. 19, the heater 14 is formed. Forming the heater 14 includes forming the metal interconnect layer 16 and forming the close contact layers 15 and 17 that cover the metal interconnect layer 16.

Figure 6:
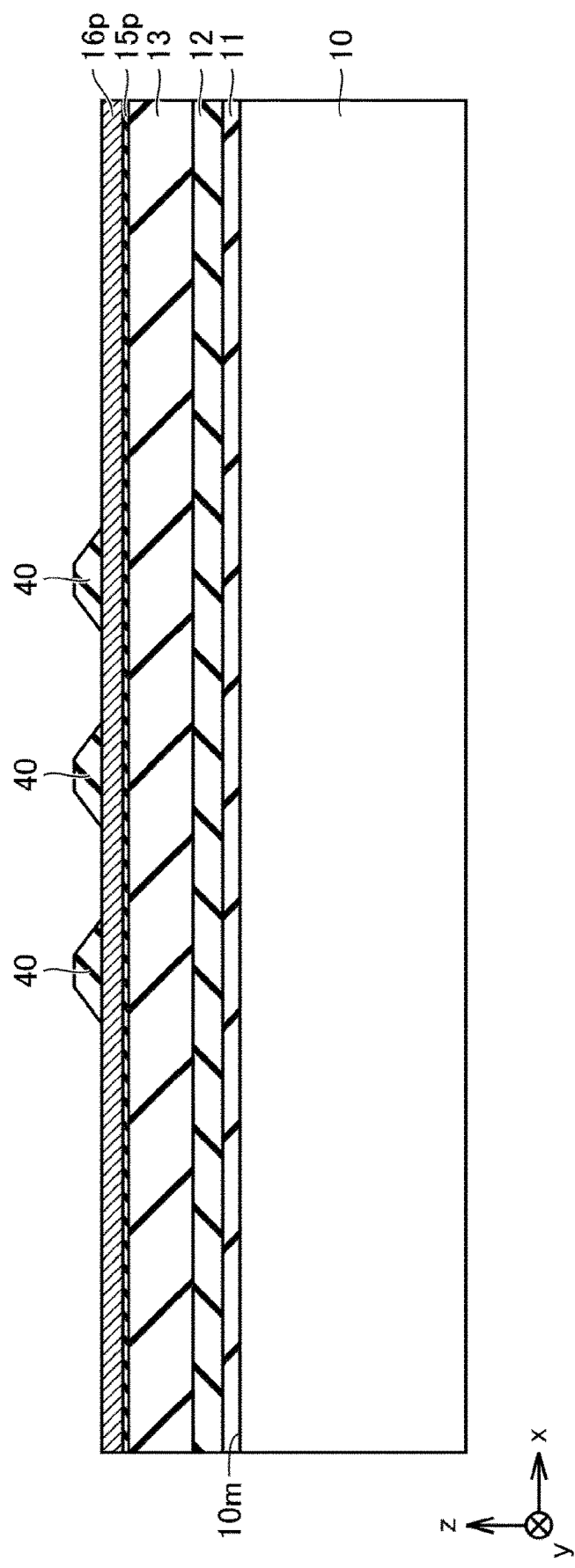
FIG. 6 is a schematic sectional view illustrating the next step of the step illustrated in FIG. 5 in the manufacturing method of the sensor of the embodiment.
Figure 7:
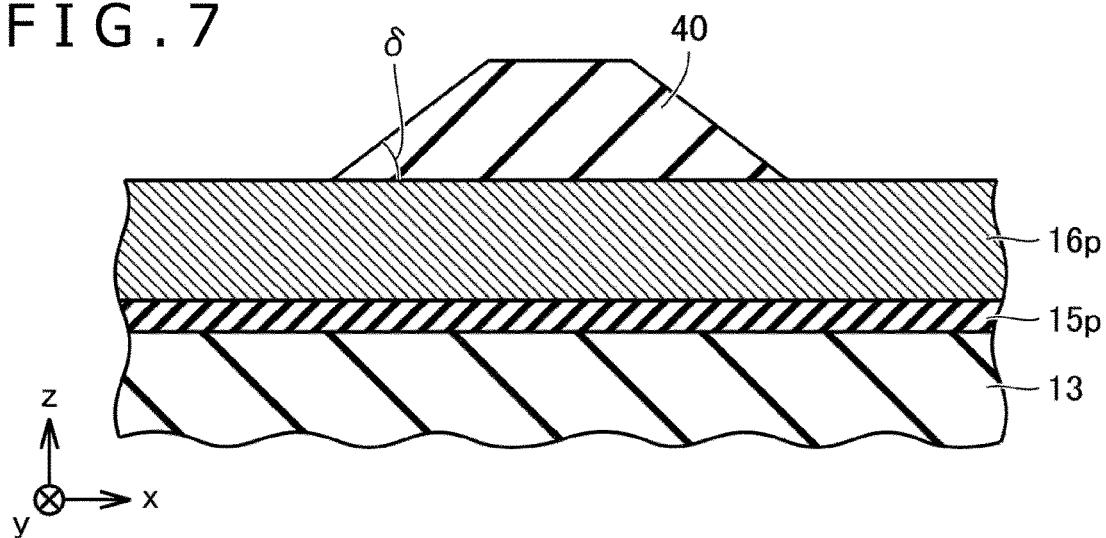
FIG. 7 is a schematic partially-enlarged sectional view of the step illustrated in FIG. 6.

Concretely, referring to FIG. 6 and FIG. 7, forming the close contact layers 15 and 17 includes forming an insulating film 15*p* on the insulating layer 13 by, for example, a sputtering method. The insulating film 15*p* is formed of a transition metal oxide such as titanium oxide, chromium oxide, tungsten oxide, molybdenum oxide, or tantalum oxide, for example.

Figure 11:
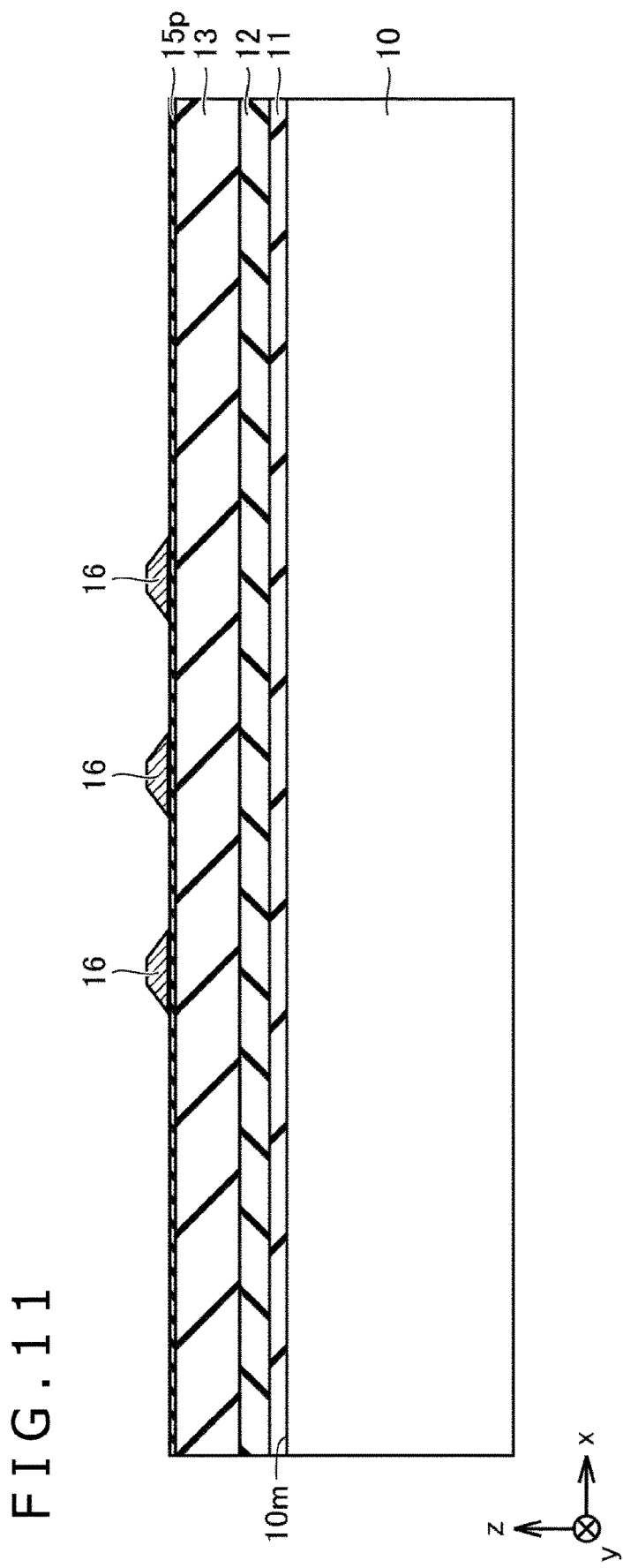
FIG. 11 is a schematic sectional view illustrating the next step of the step illustrated in FIG. 6 and FIG. 7 in the manufacturing method of the sensor of the embodiment.
Figure 12:
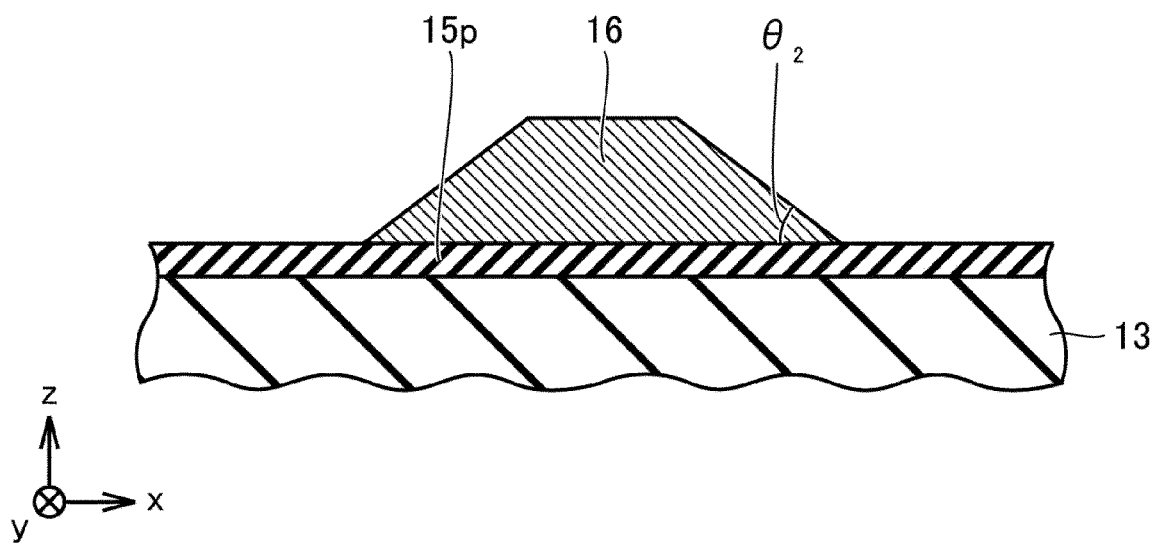
FIG. 12 is a schematic partially-enlarged sectional view of the step illustrated in FIG. 11.

Referring FIG. 11 and FIG. 12, the metal interconnect layer 16 is formed on the insulating film 15*p*. Referring FIG. 6 and FIG. 7, forming the metal interconnect layer 16 includes forming a metal film 16*p* on the insulating film 15*p* by, for example, a sputtering method. The metal film 16*p* is formed of platinum, for example. Forming the metal interconnect layer 16 further includes forming the metal interconnect layer 16 having forward tapered side surfaces by etching the metal film 16*p*.

Figure 8:
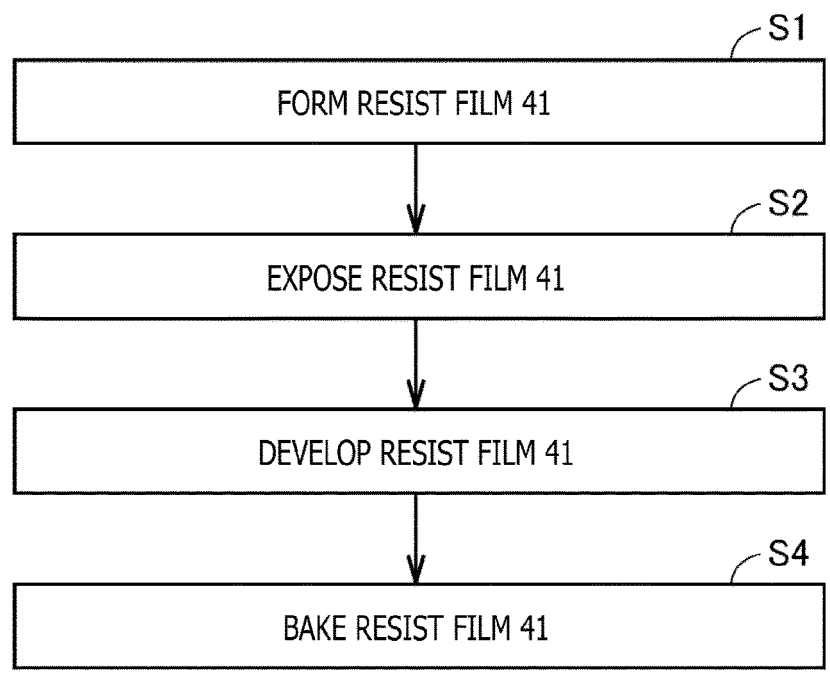
FIG. 8 is a diagram illustrating a flowchart of the step illustrated in FIG. 6 and FIG. 7.

Specifically, as illustrated in FIG. 7, a resist layer 40 is formed on the metal film 16*p*. Concretely, referring to FIG. 8, a resist film 41 is formed on the metal film 16*p* (S1). The resist film 41 is applied on the metal film 16*p* by a spin-coating method, for example. Next, referring to FIG. 8 and FIG. 10, the resist film 41 is irradiated with light 43 through a reticle 44 and a lens 45, and the resist film 41 is exposed (S2). Referring to FIG. 8, the exposed resist film 41 is developed by a developer (S3). For example, when the resist film 41 is a positive resist film, the exposed part in the resist film 41 is removed in the development step (S3). Referring to FIG. 8, the resist film 41 that remains in the development step (S3) is baked (S4). In this manner, the resist layer 40 is formed on the metal film 16*p*.

A first example of the method for forming the resist layer 40 having the forward tapered side surfaces will be described. In the first example, the resist film 41 having a low aspect ratio is formed in the development step (S3) illustrated in FIG. 8. The aspect ratio of the resist film 41 is set as low as, for example, 0.20 or lower. The aspect ratio of the resist film 41 obtained by the development step (S3) may be equal to or lower than 0.15 and may be equal to or lower than 0.10. The aspect ratio of the resist film 41 is defined as the ratio of the thickness of the resist film 41 to the width thereof. When the resist film 41 having the low aspect ratio is baked (S4), the resist film 41 contracts. When the resist film 41 contracts, tensile stress along the in-plane direction of the surface on which the resist film 41 is formed is applied to the resist film 41. A taper angle θ of the forward tapered side surfaces of the resist layer 40 can be reduced. In this manner, the resist layer 40 having the forward tapered side surfaces is obtained.

Figure 9:
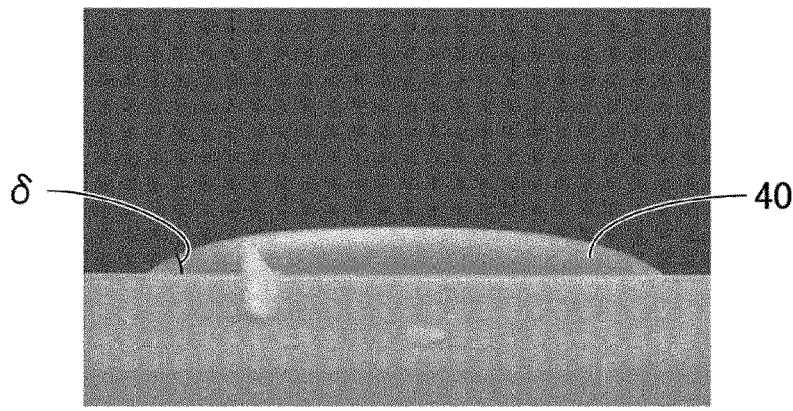
FIG. 9 is a diagram illustrating a cross-sectional scanning electron microscope (SEM) photograph of a resist layer having forward tapered side surfaces.
Figure 10:
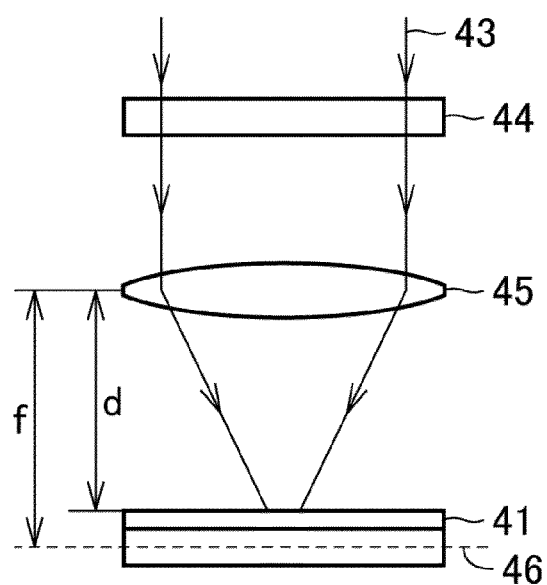
FIG. 10 is a schematic diagram illustrating an exposure step of a resist film illustrated in FIG. 8.

In FIG. 9, a photograph of Resist AZ3100 made by AZ Electronic Materials Co., Ltd after the backing step is illustrated as one concrete example of the resist layer 40 having the forward tapered side surfaces. The taper angle δ of the forward tapered side surfaces of the resist layer 40 is 36°.

A second example of the method for forming the resist layer 40 having the forward tapered side surfaces will be described. In the second example, in the exposure step (S2) illustrated in FIG. 8, the resist film 41 is disposed at a position closer to the lens 45 than a focal plane 46 of the lens 45 (see FIG. 10). An interval d between the resist film 41 and the lens 45 is shorter than a focal length f of the lens 45. As the position gets closer to the upper surface of the resist film 41, the amount of exposure of the resist film 41 increases and the rate of dissolution of the resist film 41 in the developer increases. Thus, the resist layer 40 having the forward tapered side surfaces is obtained through the development step (S3) and the post-baking step (S4).

After the resist layer 40 having the forward tapered side surfaces is formed on the metal film 16*p*, the metal film 16*p* is etched with use of the resist layer 40 as an etching mask. In this manner, the metal interconnect layer 16 (see FIG. 11 and FIG. 12) having the forward tapered side surfaces is formed. Then, the resist layer 40 that remains on the metal interconnect layer 16 is removed.

The metal film 16*p* is subjected to dry etching, for example. Specifically, the metal film 16*p* is subjected to dry etching together with part of the resist layer 40 with use of an etching gas containing an oxygen gas. The etching rate of the metal film 16*p* with respect to the etching gas is higher than the etching rate of the resist layer 40 with respect to the etching gas. As the concentration of the oxygen gas contained in the etching gas increases, the amount of resist layer 40 removed by the etching gas increases, so that the taper angle $\theta_2$ of the forward tapered side surfaces of the metal interconnect layer 16 can be decreased. The concentration of the oxygen gas contained in the etching gas is higher than 0%. The concentration of the oxygen gas contained in the etching gas may be equal to or higher than 5%. The concentration of the oxygen gas contained in the etching gas may be equal to or lower than 15%. The concentration of the oxygen gas contained in the etching gas may be equal to or lower than 10%.

Figure 13:
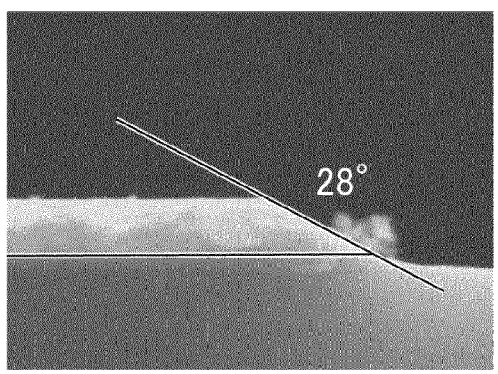
FIG. 13 is a diagram illustrating a cross-sectional SEM photograph of a metal interconnect layer having forward tapered side surfaces, obtained with use of an etching gas that is an argon gas and does not contain an oxygen gas.
Figure 14:
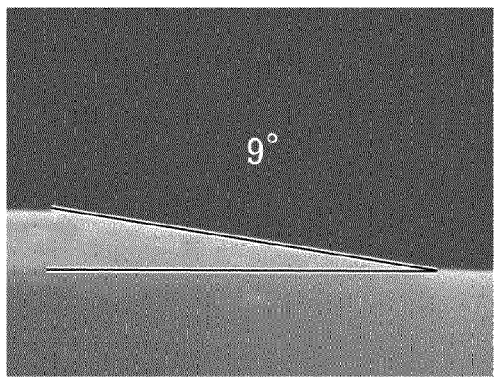
FIG. 14 is a diagram illustrating a cross-sectional SEM photograph of the metal interconnect layer having forward tapered side surfaces, obtained with use of an etching gas containing an oxygen gas at a concentration of 5% and an argon gas.
Figure 15:
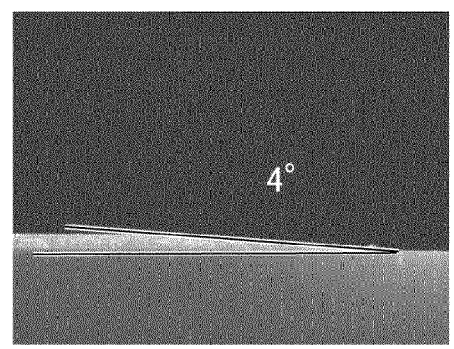
FIG. 15 is a diagram illustrating a cross-sectional SEM photograph of the metal interconnect layer having forward tapered side surfaces, obtained with use of an etching gas containing an oxygen gas at a concentration of 10% and an argon gas.
Figure 16:
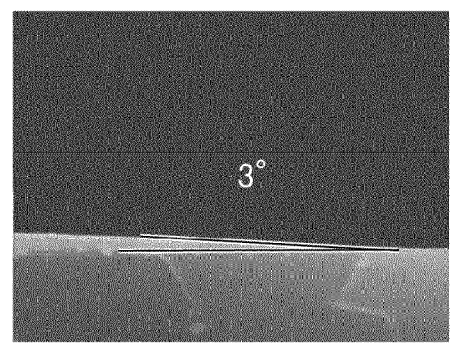
FIG. 16 is a diagram illustrating a cross-sectional SEM photograph of the metal interconnect layer having forward tapered side surfaces, obtained with use of an etching gas containing an oxygen gas at a concentration of 15% and an argon gas.

For example, as illustrated in FIG. 13, when the metal film 16*p* made of platinum is subjected to dry etching with use of an etching gas that is an argon gas and does not contain an oxygen gas, the taper angle $\theta_2$ of the forward tapered side surfaces of the metal interconnect layer 16 becomes 28°. As illustrated in FIG. 14, when the metal film 16*p* made of platinum is subjected to dry etching with use of an etching gas containing an oxygen gas at a concentration of 5% and an argon gas, the taper angle $\theta_2$ of the forward tapered side surfaces of the metal interconnect layer 16 decreases to 9°. As illustrated in FIG. 15, when the metal film 16*p* made of platinum is subjected to dry etching with use of an etching gas containing an oxygen gas at a concentration of 10% and an argon gas, the taper angle $\theta_2$ of the forward tapered side surfaces of the metal interconnect layer 16 decreases to 4°. As illustrated in FIG. 16, when the metal film 16*p* made of platinum is subjected to dry etching with use of an etching gas containing an oxygen gas at a concentration of 15% and an argon gas, the taper angle $\theta_2$ of the forward tapered side surfaces of the metal interconnect layer 16 decreases to 3°.

Figure 17:
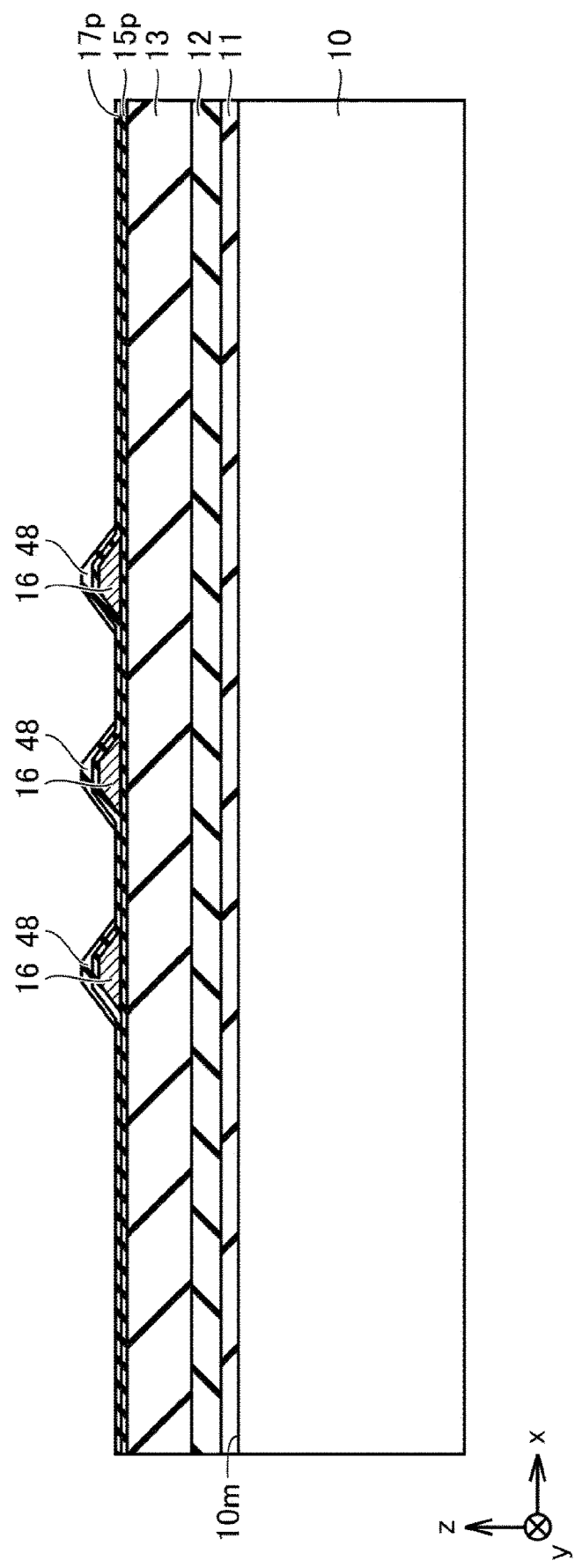
FIG. 17 is a schematic sectional view illustrating the next step of the step illustrated in FIG. 11 and FIG. 12 in the manufacturing method of the sensor of the embodiment.
Figure 18:
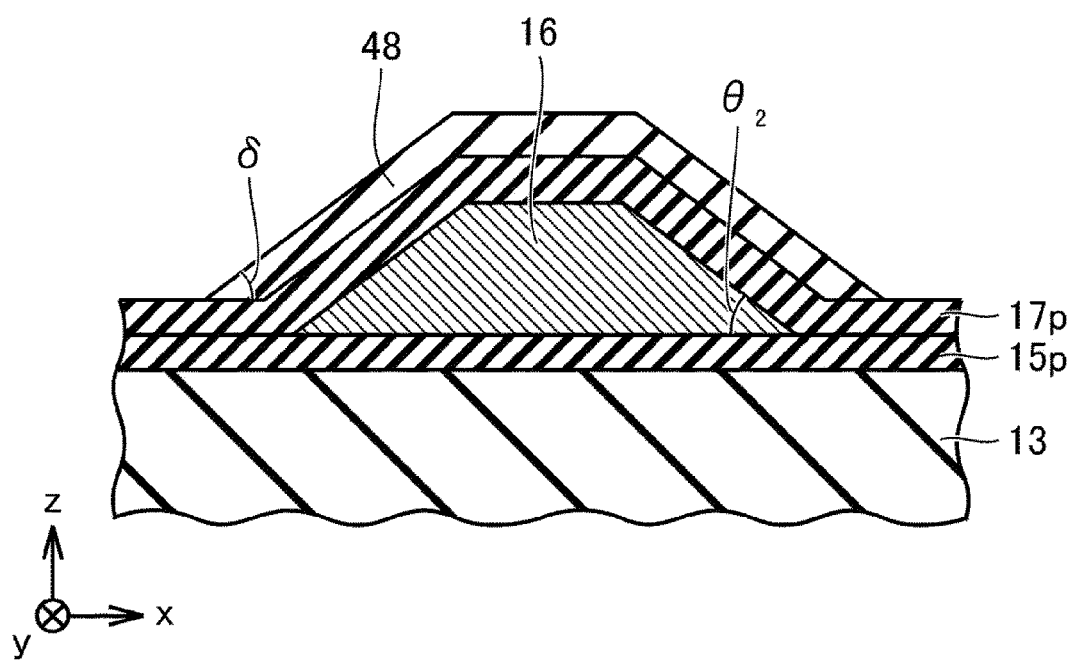
FIG. 18 is a schematic partially-enlarged sectional view of the step illustrated in FIG. 17.

Referring to FIG. 17 and FIG. 18, forming the close contact layers 15 and 17 includes forming an insulating film 17*p* on the metal interconnect layer 16 and on the insulating film 15*p* by, for example, a sputtering method. The insulating film 17*p* is formed of a transition metal oxide such as titanium oxide, chromium oxide, tungsten oxide, molybdenum oxide, or tantalum oxide, for example.

Figure 19:
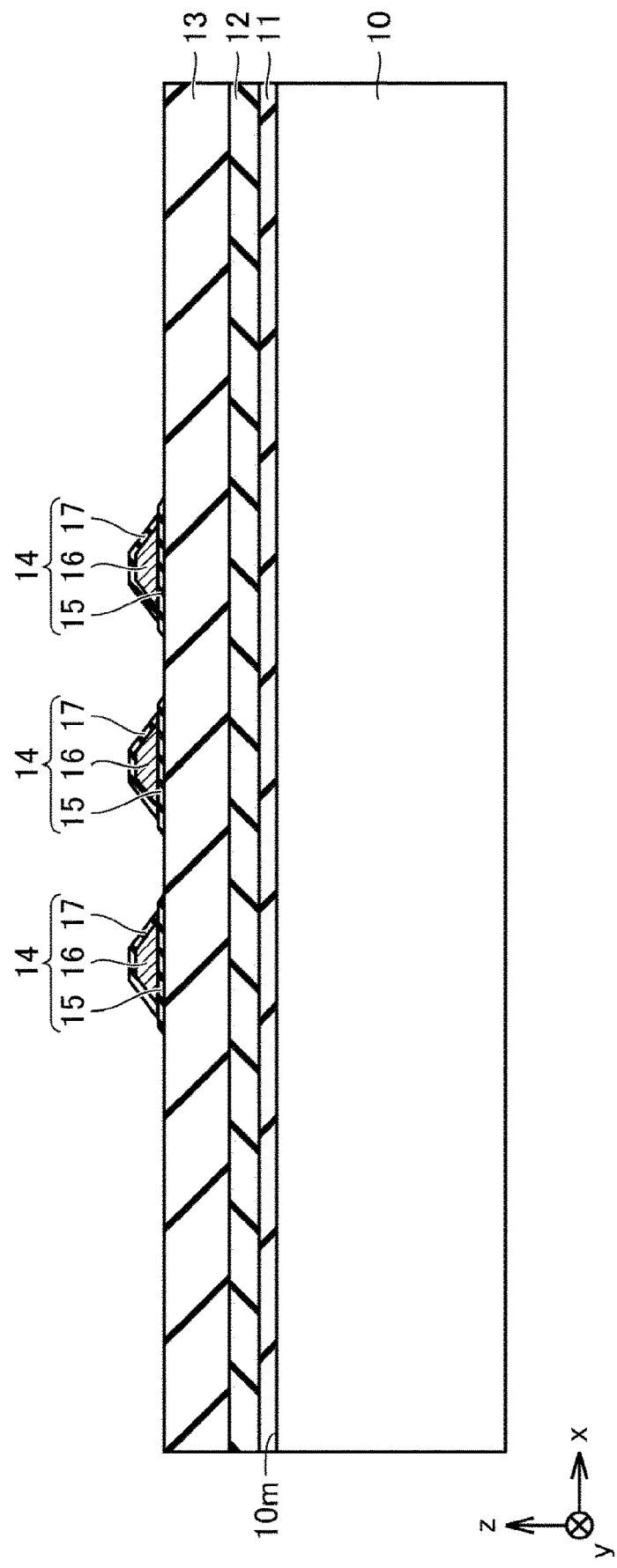
FIG. 19 is a schematic sectional view illustrating the next step of the step illustrated in FIG. 17 and FIG. 18 in the manufacturing method of the sensor of the embodiment.

Forming the close contact layers 15 and 17 includes etching the insulating films 15$p$ and 17$p$ to form the close contact layers 15 and 17 having forward tapered outer side surfaces. Specifically, as illustrated in FIG. 17 and FIG. 18, a resist layer 48 having forward tapered side surfaces is formed on the insulating film 17$p$. The resist layer 48 having the forward tapered side surfaces is formed by a method similar to that for the resist layer 40 having the forward tapered side surfaces. The insulating films 15$p$ and 17$p$ are subjected to dry etching with use of the resist layer 48 as an etching mask and with use of an etching gas such as a $Cl_2$ gas. In this manner, as illustrated in FIG. 19, the close contact layers 15 and 17 having the forward tapered outer side surfaces are formed and the heater 14 is formed.

Figure 20:
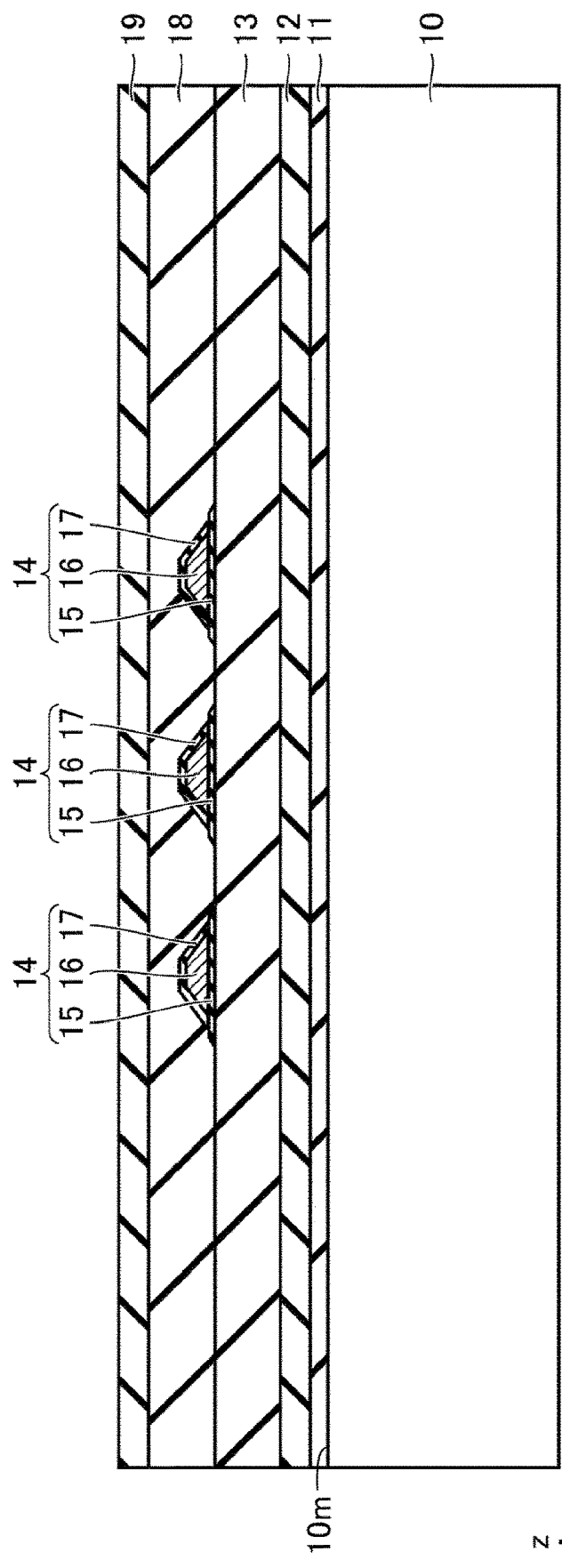
FIG. 20 is a schematic sectional view illustrating the next step of the step illustrated in FIG. 19 in the manufacturing method of the sensor of the embodiment.

Referring to FIG. 20, the insulating layer 18 is formed on the heater 14 and on the insulating layer 13 by a CVD method. The heater 14 is filled in the insulating layer 18. The insulating layer 18 is in contact with the close contact layer 17. The insulating layer 18 is formed of silicon dioxide, for example. The nitride layer 19 is formed on the insulating layer 18 by a CVD method. The nitride layer 19 is formed of silicon nitride, for example.

Referring to FIG. 21 to FIG. 25, the temperature sensor 20 is formed. Forming the temperature sensor 20 includes forming the metal interconnect layer 22 and forming the close contact layers 21 and 23 that cover the metal interconnect layer 22.

Figure 21:
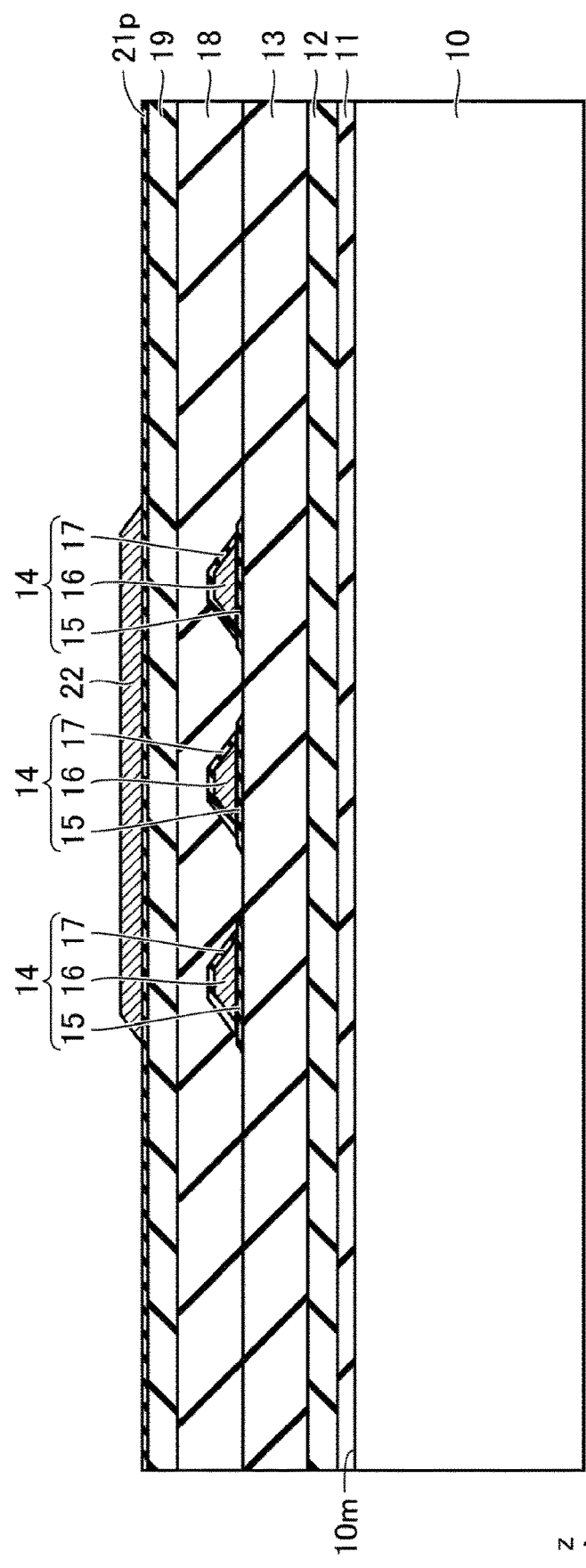
FIG. 21 is a schematic sectional view illustrating the next step of the step illustrated in FIG. 20 in the manufacturing method of the sensor of the embodiment.
Figure 22:
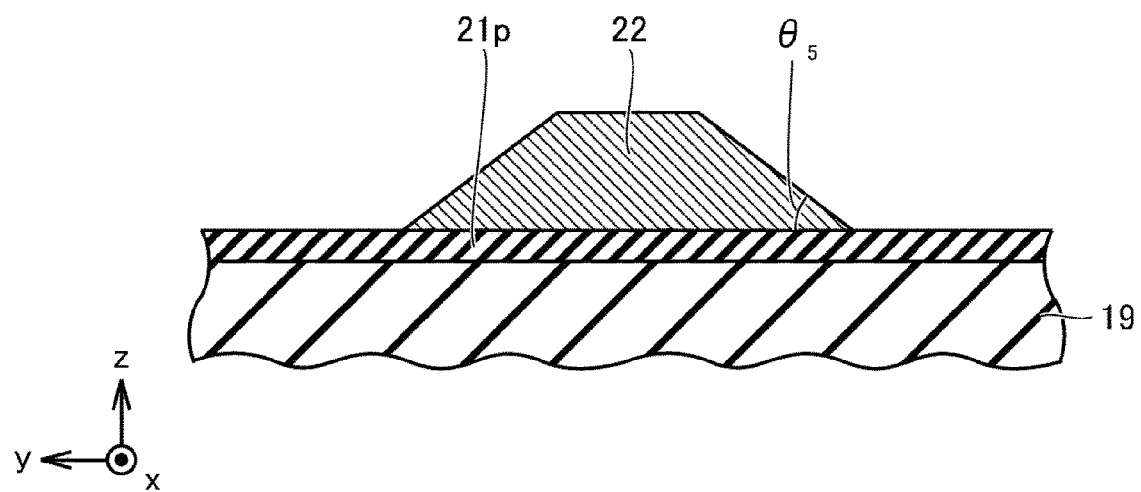
FIG. 22 is a schematic partially-enlarged sectional view of the step illustrated in FIG. 21.
Figure 23:
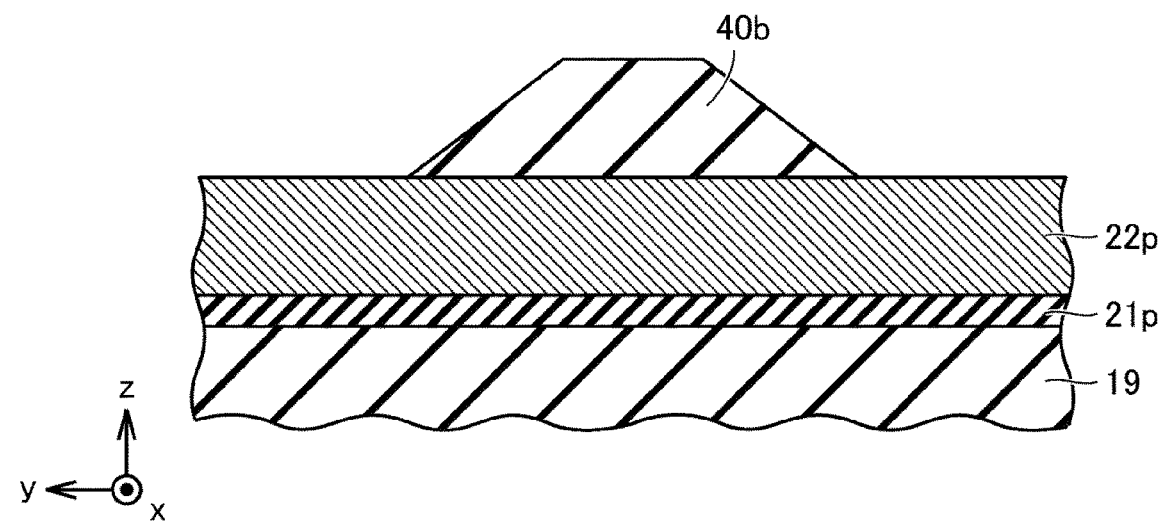
FIG. 23 is a schematic partially-enlarged sectional view illustrating one step included in the step illustrated in FIG. 21 and FIG. 22.

Concretely, referring to FIG. 21 to FIG. 23, forming the close contact layers 21 and 23 includes forming an insulating film 21$p$ on the nitride layer 19 by, for example, a sputtering method. The insulating film 21$p$ is formed of a transition metal oxide such as titanium oxide, chromium oxide, tungsten oxide, molybdenum oxide, or tantalum oxide, for example.

Referring to FIG. 21 to FIG. 23, the metal interconnect layer 22 is formed on the insulating film 21$p$. Referring to FIG. 23, forming the metal interconnect layer 22 includes forming a metal film 22$p$ on the insulating film 21$p$ by, for example, a sputtering method. The metal film 22$p$ is formed of platinum, for example. Forming the metal interconnect layer 22 further includes forming the metal interconnect layer 22 having forward tapered side surfaces by etching the metal film 22$p$.

Specifically, as illustrated in FIG. 23, a resist layer 40$b$ having forward tapered side surfaces is formed on the metal film 22$p$. The method for forming the resist layer 40$b$ having the forward tapered side surfaces is similar to the method for forming the resist layer 40 having the forward tapered side surfaces (see FIG. 8 to FIG. 10).

After the resist layer 40$b$ having the forward tapered side surfaces is formed on the metal film 22$p$, the metal film 22$p$ is etched with use of the resist layer 40$b$ as an etching mask. In this manner, the metal interconnect layer 22 (see FIG. 21 and FIG. 22) having the forward tapered side surfaces is obtained. The method for etching the metal film 22$p$ is similar to the method for etching the metal film 16$p$.

The metal film 22$p$ is subjected to dry etching, for example. Specifically, the metal film 22$p$ is subjected to dry etching together with part of the resist layer 40$b$ with use of an etching gas containing an oxygen gas. The etching rate of the metal film 22$p$ with respect to the etching gas is higher than the etching rate of the resist layer 40$b$ with respect to the etching gas. As the concentration of the oxygen gas contained in the etching gas increases, the amount of resist layer 40$b$ removed by the etching gas increases, so that the taper angle $\theta_5$ of the forward tapered side surfaces of the metal interconnect layer 22 can be decreased. The concentration of the oxygen gas contained in the etching gas is higher than 0%. The concentration of the oxygen gas contained in the etching gas may be equal to or higher than 5%. The concentration of the oxygen gas contained in the etching gas may be equal to or lower than 15%. The concentration of the oxygen gas contained in the etching gas may be equal to or lower than 10%.

Figure 25:
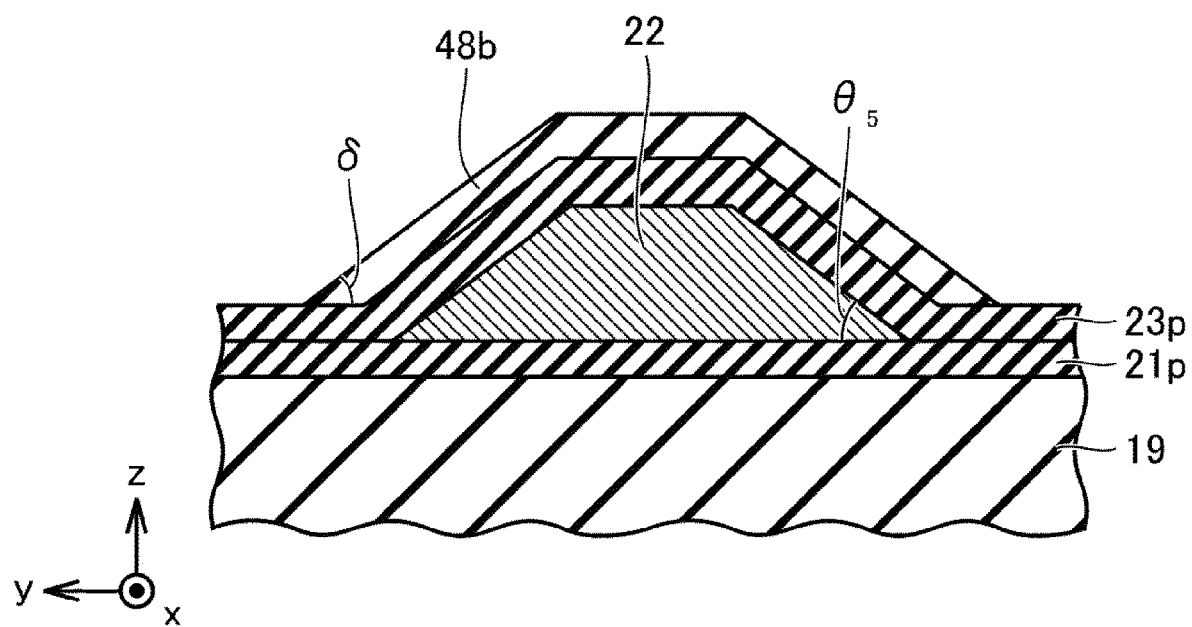
FIG. 25 is a schematic partially-enlarged sectional view illustrating one step included in the step illustrated in FIG. 24.

Referring to FIG. 25, forming the close contact layers 21 and 23 includes forming an insulating film 23$p$ on the metal interconnect layer 22 and on the insulating film 21$p$ by, for example, a sputtering method. The insulating film 23$p$ is formed of a transition metal oxide such as titanium oxide, chromium oxide, tungsten oxide, molybdenum oxide, or tantalum oxide, for example.

Figure 24:
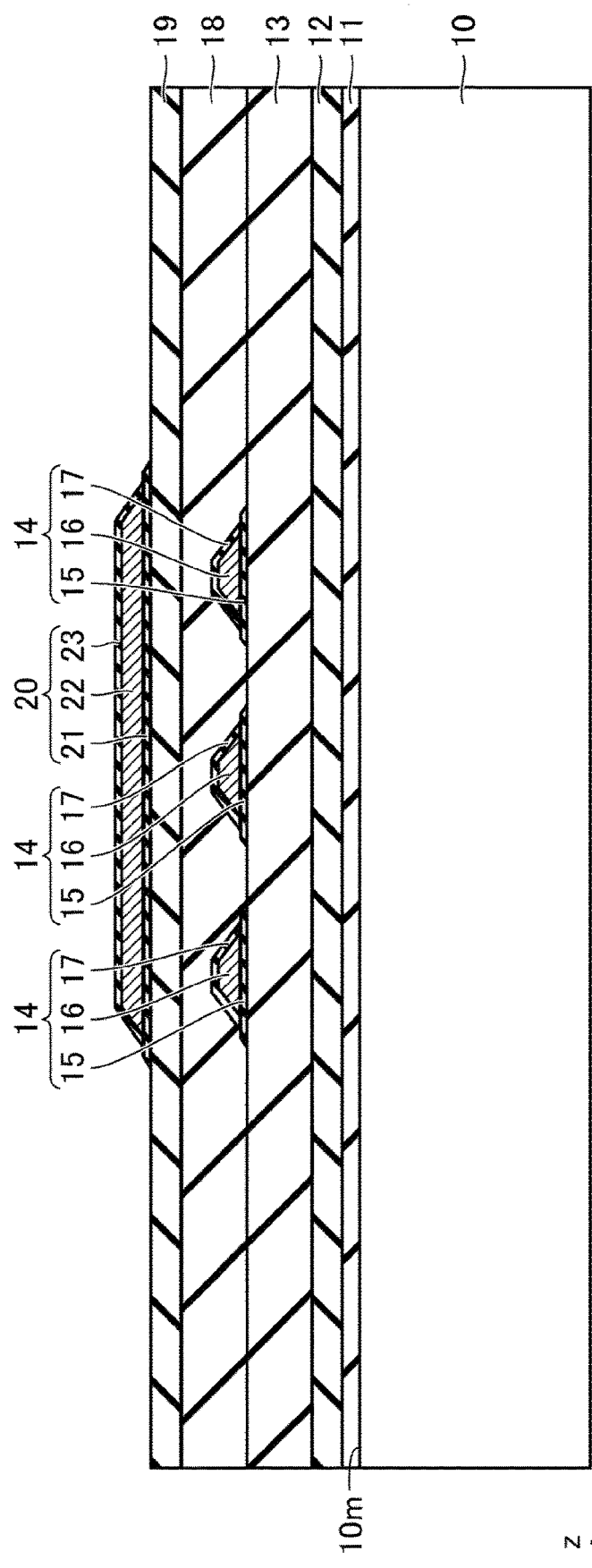
FIG. 24 is a schematic sectional view illustrating the next step of the step illustrated in FIG. 21 and FIG. 22 in the manufacturing method of the sensor of the embodiment.

Forming the close contact layers 21 and 23 includes etching the insulating films 21$p$ and 23$p$ to form the close contact layers 21 and 23 having forward tapered outer side surfaces. Specifically, as illustrated in FIG. 25, a resist layer 48$b$ having forward tapered side surfaces is formed on the insulating film 23$p$. The resist layer 48$b$ having the forward tapered side surfaces is formed by a method similar to that for the resist layer 48 having the forward tapered side surfaces. The insulating films 21$p$ and 23$p$ are subjected to dry etching with use of the resist layer 48$b$ as an etching mask and with use of an etching gas such as a $Cl_2$ gas. In this manner, as illustrated in FIG. 24, the close contact layers 21 and 23 having the forward tapered outer side surfaces are formed, and the temperature sensor 20 is formed.

Figure 26:
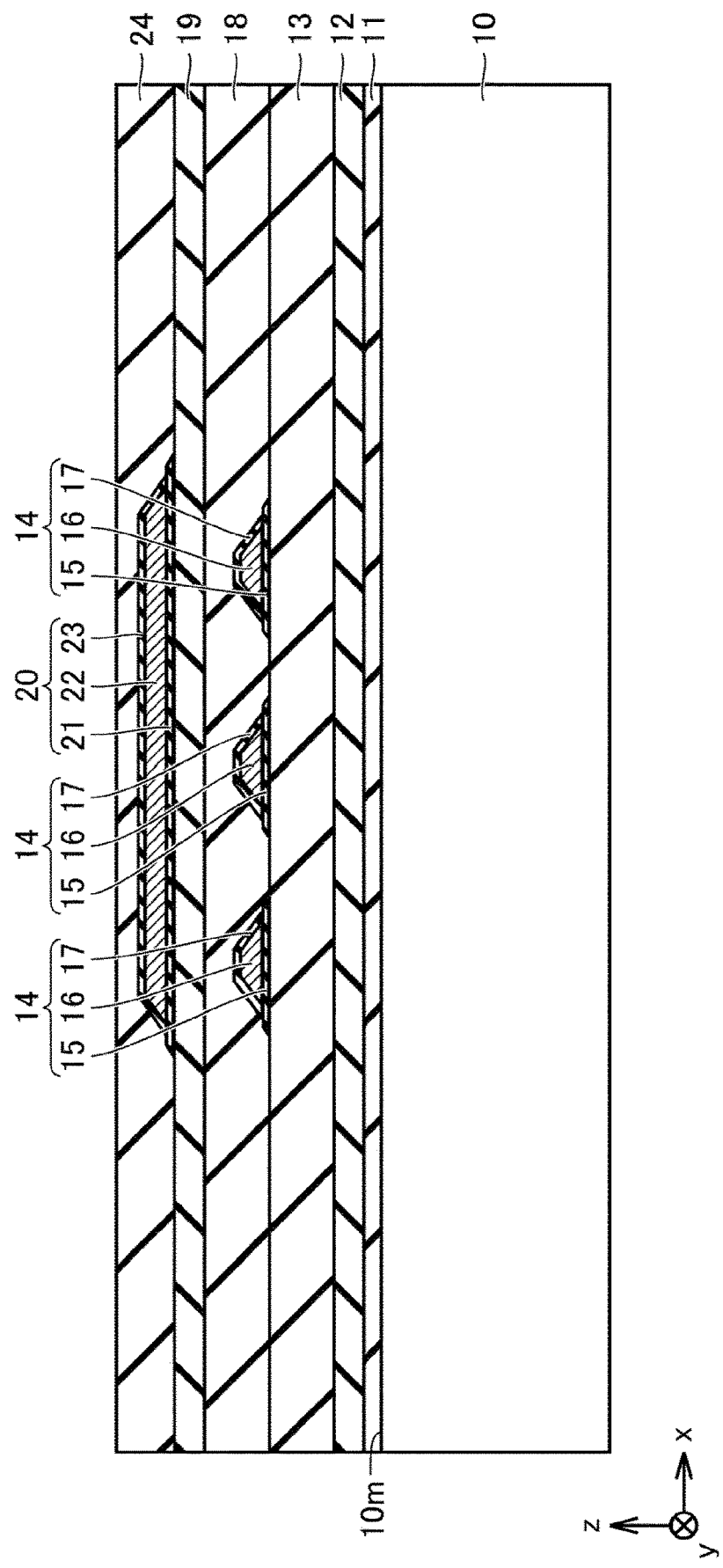
FIG. 26 is a schematic sectional view illustrating the next step of the step illustrated in FIG. 24 in the manufacturing method of the sensor of the embodiment.

Referring to FIG. 26, the insulating layer 24 is formed on the temperature sensor 20 and on the nitride layer 19 by a CVD method. The temperature sensor 20 is filled in the insulating layer 24. The insulating layer 24 is in contact with the close contact layer 23. The insulating layer 24 is formed of silicon dioxide, for example.

Figure 27:
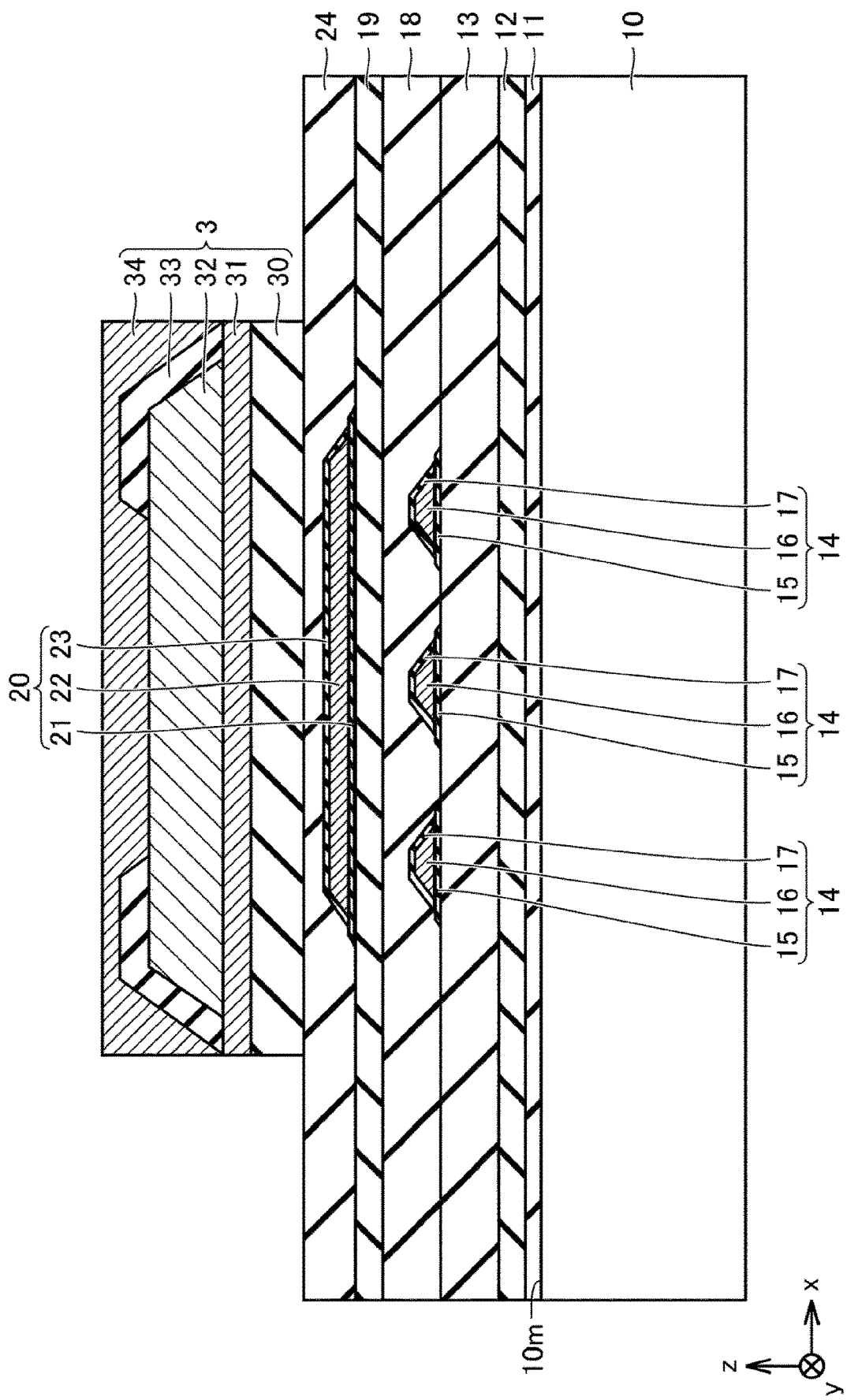
FIG. 27 is a schematic sectional view illustrating the next step of the step illustrated in FIG. 26 in the manufacturing method of the sensor of the embodiment.

Referring to FIG. 27, the sensor part 3 is formed.

Concretely, the gas flow path 30 is formed on the insulating layer 24. The gas flow path 30 is formed of a porous material. Specifically, the gas flow path 30 is formed of a porous transition metal oxide. The porous transition metal oxide is tantalum pentoxide ($Ta_2O_5$), titanium dioxide ($TiO_2$), or chromium oxide (III) ($Cr_2O_3$), for example. The gas flow path 30 is formed by an oblique evaporation method such as a rotational oblique evaporation method, for example.

The first porous electrode 31 is formed on the gas flow path 30. The first porous electrode 31 is in contact with the gas flow path 30. The first porous electrode 31 is formed by a sputtering method, for example. The first porous electrode 31 is a porous metal layer, for example. The first porous electrode 31 is formed of platinum (Pt) or palladium (Pd), for example.

The solid electrolyte layer 32 is formed on the first porous electrode 31. The solid electrolyte layer 32 is in contact with the first porous electrode 31. The solid electrolyte layer 32 is formed by a sputtering method, for example. For example, the solid electrolyte layer 32 is a layer in which CaO, MgO, $Y_2O_3$, $Yb_2O_3$, or other substances is added as a stabilizer to a base material such as $ZrO_2$, $HfO_2$, $ThO_2$, or $Bi_2O_3$. Specifically, the solid electrolyte layer 32 is formed of yttria-stabilized zirconia (YSZ).

The insulating layer 33 is formed on the solid electrolyte layer 32 and on the first porous electrode 31 by a CVD method. The insulating layer 33 is formed of silicon dioxide, for example. The surface of part of the solid electrolyte layer 32 is exposed from the insulating layer 33.

Subsequently, the second porous electrode 34 is formed on the solid electrolyte layer 32 and on the insulating layer 33. The second porous electrode 34 is in contact with the surface of the solid electrolyte layer 32 exposed from the insulating layer 33. The second porous electrode 34 is formed by a sputtering method, for example. The second porous electrode 34 is a porous metal layer, for example. The second porous electrode 34 is formed of platinum (Pt) or palladium (Pd), for example. The second porous electrode 34 is electrically insulated from the first porous electrode 31 by the insulating layer 33. In this manner, the sensor part 3 is formed.

Figure 28:
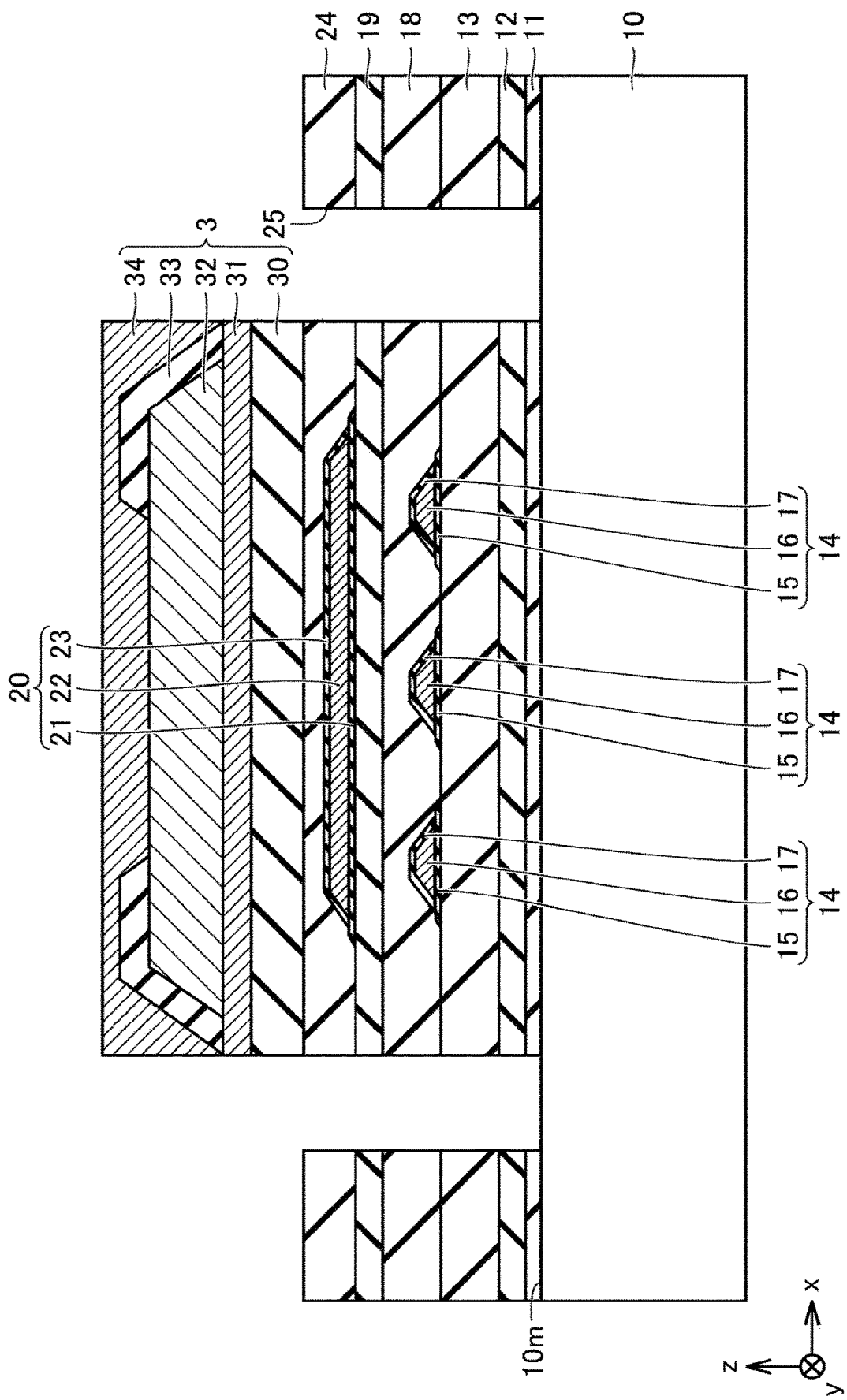
FIG. 28 is a schematic sectional view illustrating the next step of the step illustrated in FIG. 27 in the manufacturing method of the sensor of the embodiment.

Referring to FIG. 28, the opening 25 that reaches the major surface 10m of the substrate 10 is formed in the multilayer structure including the insulating layers 11, 13, 18, and 24 and the nitride layers 12 and 19. The opening 25 is formed by executing dry etching of the multilayer structure including the insulating layers 11, 13, 18, and 24 and the nitride layers 12 and 19 with use of an etching gas such as a $CF_4$ gas.

Then, the opening 10a is made in the substrate 10 by executing dry etching of part of the substrate 10 with use of an etching gas such as an $SF_6$ gas, a $C_4F_8$ gas, or a mixture gas of them. The opening 10a communicates with the opening 25. In plan view of the major surface 10m of the substrate 10, the heater 14 is surrounded by the edge of the opening 10a. In this manner, the sensor 1 illustrated in FIG. 1 to FIG. 4 is obtained.

Figure 29:
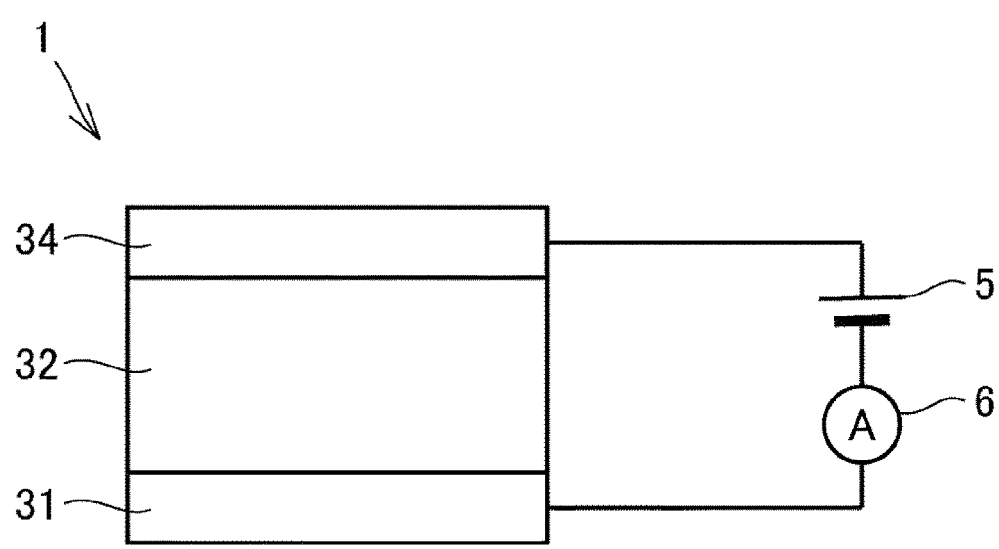
FIG. 29 is a circuit diagram of the sensor of the embodiment.

With reference to FIG. 1, FIG. 2, and FIG. 29, operation of the sensor 1 will be described by taking as an example the case in which the gas is the exhaust gas of an automobile and a component gas contained in the gas is nitrogen oxides ($NO_X$).

The gas passes through the gas flow path 30 and the first porous electrode 31 from the gas inlet (not illustrated) and flows to the solid electrolyte layer 32. The gas flow path 30 limits the amount of flow of the gas to the solid electrolyte layer 32 per unit time. The first porous electrode 31 decomposes nitric oxide NO, which occupies a large part of the nitrogen oxides ($NO_X$) contained in the gas, into nitrogen ($N_2$) and oxygen ($O_2$).

As illustrated in FIG. 29, the first porous electrode 31 is connected to a negative electrode of a voltage source 5. The oxygen ($O_2$) receives electrons supplied from the voltage source 5 at the interface between the first porous electrode 31 and the solid electrolyte layer 32 and is converted to oxygen ions ($2O^{2-}$). The solid electrolyte layer 32 is being heated at a temperature of, for example, at least 400° C. and at most 750° C. by using the heater 14. The oxygen ions are conducted from a first surface of the solid electrolyte layer 32 close to the first porous electrode 31 to a second surface of the solid electrolyte layer 32 close to the second porous electrode 34. Due to the conduction of the oxygen ions, a current flows between the first porous electrode 31 and the second porous electrode 34.

Because the flow rate of the gas to the solid electrolyte layer 32 is limited by the gas flow path 30, the current that flows between the first porous electrode 31 and the second porous electrode 34 is constant even when the voltage between the first porous electrode 31 and the second porous electrode 34 is increased. This constant current is referred to as the limiting current. The limiting current value is proportional to the concentration of a component gas (for example, nitrogen oxides ($NO_X$)) contained in the gas (for example, exhaust gas). The limiting current value is measured by a current detector 6. The concentration of a component gas contained in the gas is obtained from the limiting current value. The voltage source 5 may be a variable voltage source. By changing the magnitude of the voltage applied between the first porous electrode 31 and the second porous electrode 34, another limiting current value corresponding to another component gas (for example, water vapor ($H_2O$) or oxygen ($O_2$)) contained in the gas can be obtained. From the other limiting current value, the concentration of the other component gas (for example, water vapor ($H_2O$) or oxygen ($O_2$)) can be obtained.

The oxygen ions ($2O^{2-}$) that have reached the second porous electrode 34 are deprived of electrons at the interface between the second porous electrode 34 and the solid electrolyte layer 32 and are converted to oxygen ($O_2$). The exhaust gas such as the oxygen ($O_2$) is released from the second porous electrode 34.

Modification Examples

Figure 30:
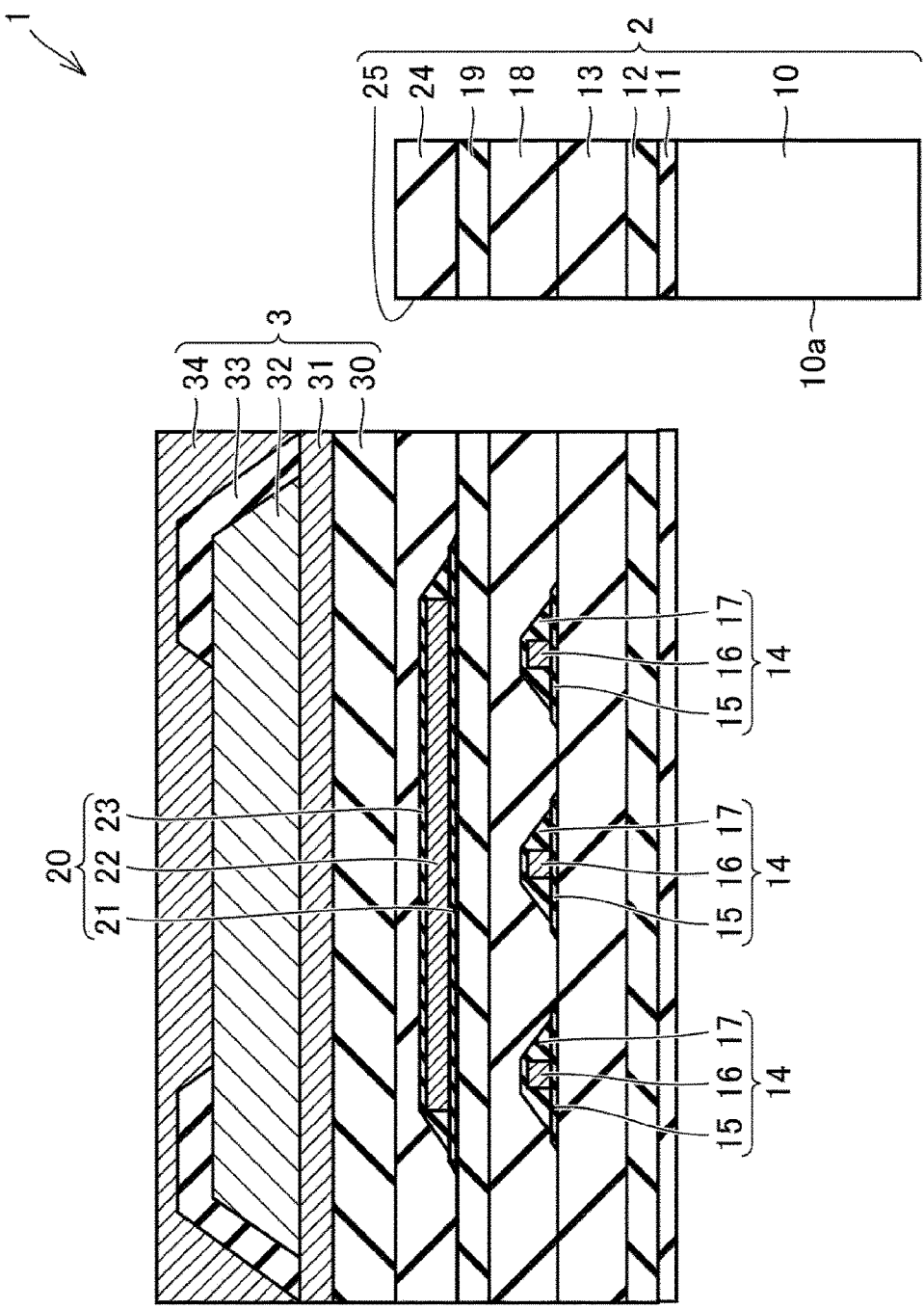
FIG. 30 is a schematic sectional view of a first modification example of the embodiment.

Referring to FIG. 30, in a first modification example of the present embodiment, at least one of the metal interconnect layer 16 of the heater 14 or the metal interconnect layer 22 of the temperature sensor 20 may have side surfaces perpendicular to the surface on which at least one of the metal interconnect layer 16 or the metal interconnect layer 22 is formed instead of having forward tapered side surfaces. Specifically, a configuration may be employed in which the metal interconnect layer 16 of the heater 14 and the metal interconnect layer 22 of the temperature sensor 20 do not have forward tapered side surfaces, and the metal interconnect layer 16 has side surfaces perpendicular to the surface on which the metal interconnect layer 16 is formed, and the metal interconnect layer 22 has side surfaces perpendicular to the surface on which the metal interconnect layer 22 is formed.

Referring to FIG. 31, in a second modification example of the present embodiment, at least one of the close contact layers 15 and 17 of the heater 14 or the close contact layers 21 and 23 of the temperature sensor 20 may be omitted. Specifically, both the close contact layers 15 and 17 of the heater 14 and the close contact layers 21 and 23 of the temperature sensor 20 may be omitted. In the second modification example of the present embodiment, the taper angle $\theta_1$ (see FIG. 3) of the forward tapered side surfaces of the heater interconnect is given by the taper angle $\theta_2$ (see FIG. 3) of the forward tapered side surfaces of the metal interconnect layer 16. The taper angle $\theta_4$ (see FIG. 4) of the forward tapered side surfaces of the temperature sensor interconnect is given by the taper angle $\theta_5$ (see FIG. 4) of the forward tapered side surfaces of the metal interconnect layer 22.

The sensor 1 is not limited to the limiting current-type sensor and may be a gas sensor such as a gas flow velocity sensor that measures the flow velocity of a gas. Depending on the kind of sensor part 3, one of the heater 14 or the temperature sensor 20 may be omitted. That is, it suffices that the sensor 1 includes at least one of the heater 14 or temperature sensor 20.

Effects of the sensor 1 of the present embodiment and the manufacturing method thereof will be described.

The sensor 1 of the present embodiment includes the substrate 10 including the major surface 10m, the sensor part 3 including the gas flow path 30 formed of a porous material, and at least one of the heater 14 or the temperature sensor 20. The heater 14 can heat the sensor part 3. The temperature sensor 20 can measure the temperature of the sensor part 3. The sensor part 3 and the at least one of the heater 14 or the temperature sensor 20 are stacked over the major surface 10m of the substrate 10. The at least one of the heater 14 or the temperature sensor 20 is the interconnect (at least one of the heater interconnect or the temperature sensor interconnect) having forward tapered side surfaces. The at least one of the heater 14 or the temperature sensor 20 includes the metal interconnect layer (at least one of the metal interconnect layer 16 or the metal interconnect layer 22). In plan view of the major surface 10m of the substrate 10, the forward tapered side surfaces of the interconnect overlap with the gas flow path 30.

The at least one of the heater 14 or the temperature sensor 20 is the interconnect (at least one of the heater interconnect or the temperature sensor interconnect) having the forward tapered side surfaces. Thus, although the forward tapered side surfaces of the interconnect overlap with the gas flow path 30 in plan view of the major surface 10m of the substrate 10, steps in the surface on which the gas flow path 30 is formed can be made gentle. Disconnection of the gas flow path 30 and an excessive rise in the film density of the gas flow path 30 are prevented, and the gas flow path 30 having high quality can be stably formed. Variation in characteristics of the sensor 1 can be reduced.

In the sensor 1 of the present embodiment, the taper angle (at least one of the taper angle $\theta_1$ or the taper angle $\theta_4$) of the forward tapered side surfaces of the interconnect (at least one of the heater interconnect or the temperature sensor interconnect) is equal to or smaller than 45°. Thus, steps in the surface on which the gas flow path 30 is formed can be made gentle. The gas flow path 30 having high quality can be stably formed. Variation in characteristics of the sensor 1 can be reduced.

In the sensor 1 of the present embodiment, the taper angle (at least one of the taper angle $\theta_1$ or the taper angle $\theta_4$) of the forward tapered side surfaces of the interconnect (at least one of the heater interconnect or the temperature sensor interconnect) is equal to or smaller than 20°. Thus, steps in the surface on which the gas flow path 30 is formed can be made gentle. The gas flow path 30 having high quality can be stably formed. Variation in characteristics of the sensor 1 can be reduced.

In the sensor 1 of the present embodiment, the metal interconnect layer (at least one of the metal interconnect layer 16 or the metal interconnect layer 22) has forward tapered side surfaces. In plan view of the major surface 10m of the substrate 10, the forward tapered side surfaces of the metal interconnect layer overlap with the gas flow path 30.

The metal interconnect layer (at least one of the metal interconnect layer 16 or the metal interconnect layer 22) has the forward tapered side surfaces. Thus, although the forward tapered side surfaces of the metal interconnect layer overlap with the gas flow path 30 in plan view of the major surface 10m of the substrate 10, steps in the surface on which the gas flow path 30 is formed can be made gentle. Disconnection of the gas flow path 30 and an excessive rise in the film density of the gas flow path 30 are prevented, and the gas flow path 30 having high quality can be stably formed. Variation in characteristics of the sensor 1 can be reduced.

In the sensor 1 of the present embodiment, the taper angle (at least one of the taper angle $\theta_2$ or the taper angle $\theta_5$) of the forward tapered side surfaces of the metal interconnect layer (at least one of the metal interconnect layer 16 or the metal interconnect layer 22) is equal to or smaller than 45°. Thus, steps in the surface on which the gas flow path 30 is formed can be made gentle. The gas flow path 30 having high quality can be stably formed. Variation in characteristics of the sensor 1 can be reduced.

In the sensor 1 of the present embodiment, the taper angle (at least one of the taper angle $\theta_2$ or the taper angle $\theta_5$) of the forward tapered side surfaces of the metal interconnect layer (at least one of the metal interconnect layer 16 or the metal interconnect layer 22) is equal to or smaller than 20°. Thus, steps in the surface on which the gas flow path 30 is formed can be made gentle. The gas flow path 30 having high quality can be stably formed. Variation in characteristics of the sensor 1 can be reduced.

The sensor 1 of the present embodiment further includes the insulating layer (at least one of the insulating layer 18 or the insulating layer 24) in which the at least one of the heater 14 or the temperature sensor 20 is filled. The at least one of the heater 14 or the temperature sensor 20 further includes the close contact layer (at least one of the close contact layer 17 or the close contact layer 23) that covers the metal interconnect layer (at least one of the metal interconnect layer 16 or the metal interconnect layer 22). The close contact layer has forward tapered outer side surfaces in contact with the insulating layer. In plan view of the major surface 10m of the substrate 10, the outer side surfaces of the close contact layer overlap with the gas flow path 30.

The close contact layer (at least one of the close contact layer 17 or the close contact layer 23) has the forward tapered outer side surfaces. Thus, although the forward tapered outer side surfaces of the close contact layer overlap with the gas flow path 30 in plan view of the major surface 10m of the substrate 10, steps in the surface on which the gas flow path 30 is formed can be made gentle. Disconnection of the gas flow path 30 and an excessive rise in the film density of the gas flow path 30 are prevented, and the gas flow path 30 having high quality can be stably formed. Variation in characteristics of the sensor 1 can be reduced. Furthermore, the close contact layer improves close contact between the metal interconnect layer (at least one of the metal interconnect layer 16 or the metal interconnect layer 22) and the insulating layer (at least one of the insulating layer 18 or the insulating layer 24). Separation of the insulating layer from the metal interconnect layer can be prevented. Variation in characteristics of the sensor 1 can be reduced.

In the sensor 1 of the present embodiment, the taper angle (at least one of the taper angle $\theta_3$ or the taper angle $\theta_6$) of the outer side surfaces of the close contact layer (at least one of the close contact layer 17 or the close contact layer 23) is equal to or smaller than 45°. Thus, steps in the surface on which the gas flow path 30 is formed can be made gentle. The gas flow path 30 having high quality can be stably formed. Variation in characteristics of the sensor 1 can be reduced.

In the sensor 1 of the present embodiment, the taper angle (at least one of the taper angle $\theta_3$ or the taper angle $\theta_6$) of the outer side surfaces of the close contact layer (at least one of the close contact layer 17 or the close contact layer 23) is equal to or smaller than 20°. Thus, steps in the surface on which the gas flow path 30 is formed can be made gentle. The gas flow path 30 having high quality can be stably formed. Variation in characteristics of the sensor 1 can be reduced.

In the sensor 1 of the present embodiment, the gas flow path 30 is formed of a porous transition metal oxide. Thus, even when the sensor 1 is operated at a high temperature while the sensor part 3 is heated by the heater 14, pores of the gas flow path 30 formed of the porous transition metal oxide hardly aggregate. Variation in characteristics of the sensor 1 can be reduced.

In the sensor 1 of the present embodiment, the sensor part 3 further includes the porous electrode (first porous electrode 31) formed on the gas flow path 30 and the solid electrolyte layer 32 in contact with the porous electrode. In plan view of the major surface 10*m* of the substrate 10, the forward tapered side surfaces of the interconnect (at least one of the heater interconnect or the temperature sensor interconnect) overlap with the solid electrolyte layer 32. Thus, variation in characteristics of the sensor 1 that is a limiting current-type gas sensor can be reduced.

The manufacturing method of the sensor 1 of the present embodiment includes forming at least one of the heater 14 or the temperature sensor 20 and forming the sensor part 3 including the gas flow path 30 formed of a porous material. The heater 14 can heat the sensor part 3. The temperature sensor 20 can measure the temperature of the sensor part 3. The sensor part 3 and the at least one of the heater 14 or the temperature sensor 20 are stacked over the major surface 10*m* of the substrate 10. The at least one of the heater 14 or the temperature sensor 20 is the interconnect (at least one of the heater interconnect or the temperature sensor interconnect) having forward tapered side surfaces. The forming the at least one of the heater 14 or the temperature sensor 20 includes forming the metal interconnect layer (at least one of the metal interconnect layer 16 or the metal interconnect layer 22). In plan view of the major surface 10*m* of the substrate 10, the forward tapered side surfaces of the interconnect (at least one of the heater interconnect or the temperature sensor interconnect) overlap with the gas flow path 30.

The at least one of the heater 14 or the temperature sensor 20 is the interconnect (at least one of the heater interconnect or the temperature sensor interconnect) having the forward tapered side surfaces. Thus, although the forward tapered side surfaces of the interconnect overlap with the gas flow path 30 in plan view of the major surface 10*m* of the substrate 10, steps in the surface on which the gas flow path 30 is formed can be made gentle. Disconnection of the gas flow path 30 and an excessive rise in the film density of the gas flow path 30 are prevented, and the gas flow path 30 having high quality can be stably formed. The sensor 1 in which variation in characteristics is reduced can be obtained.

In the manufacturing method of the sensor 1 of the present embodiment, the taper angle (at least one of the taper angle $\theta_1$ or the taper angle $\theta_4$) of the forward tapered side surfaces of the interconnect (at least one of the heater interconnect or the temperature sensor interconnect) is equal to or smaller than 45°. Thus, steps in the surface on which the gas flow path 30 is formed can be made gentle. The gas flow path 30 having high quality can be stably formed. The sensor 1 in which variation in characteristics is reduced can be obtained.

In the manufacturing method of the sensor 1 of the present embodiment, the taper angle (at least one of the taper angle $\theta_1$ or the taper angle $\theta_4$) of the forward tapered side surfaces of the interconnect (at least one of the heater interconnect or the temperature sensor interconnect) is equal to or smaller than 20°. Thus, steps in the surface on which the gas flow path 30 is formed can be made gentle. The gas flow path 30 having high quality can be stably formed. The sensor 1 in which variation in characteristics is reduced can be obtained.

In the manufacturing method of the sensor 1 of the present embodiment, the forming the metal interconnect layer (at least one of the metal interconnect layer 16 or the metal interconnect layer 22) includes forming the metal film (at least one of the metal film 16*p* or the metal film 22*p*) and forming the metal interconnect layer having forward tapered side surfaces by etching the metal film. In plan view of the major surface 10*m* of the substrate 10, the forward tapered side surfaces of the metal interconnect layer overlap with the gas flow path 30.

The metal interconnect layer (at least one of the metal interconnect layer 16 or the metal interconnect layer 22) has the forward tapered side surfaces. Thus, although the forward tapered side surfaces of the metal interconnect layer overlap with the gas flow path 30 in plan view of the major surface 10*m* of the substrate 10, steps in the surface on which the gas flow path 30 is formed can be made gentle. Disconnection of the gas flow path 30 and an excessive rise in the film density of the gas flow path 30 are prevented, and the gas flow path 30 having high quality can be stably formed. The sensor 1 in which variation in characteristics is reduced can be obtained.

In the manufacturing method of the sensor 1 of the present embodiment, the taper angle (at least one of the taper angle $\theta_2$ or the taper angle $\theta_5$) of the forward tapered side surfaces of the metal interconnect layer (at least one of the metal interconnect layer 16 or the metal interconnect layer 22) is equal to or smaller than 45°. Thus, steps in the surface on which the gas flow path 30 is formed can be made gentle. The gas flow path 30 having high quality can be stably formed. The sensor 1 in which variation in characteristics is reduced can be obtained.

In the manufacturing method of the sensor 1 of the present embodiment, the taper angle (at least one of the taper angle $\theta_2$ or the taper angle $\theta_5$) of the forward tapered side surfaces of the metal interconnect layer (at least one of the metal interconnect layer 16 or the metal interconnect layer 22) is equal to or smaller than 20°. Thus, steps in the surface on which the gas flow path 30 is formed can be made gentle. The gas flow path 30 having high quality can be stably formed. The sensor 1 in which variation in characteristics is reduced can be obtained.

In the manufacturing method of the sensor 1 of the present embodiment, the forming the metal interconnect layer (at least one of the metal interconnect layer 16 or the metal interconnect layer 22) further includes forming a first resist layer (at least one of the resist layer 40 or the resist layer 40*b*) having forward tapered side surfaces on the metal film (at least one of the metal film 16*p* or the metal film 22*p*). The metal film is etched with use of the first resist layer as a first etching mask.

Thus, the metal interconnect layer (at least one of the metal interconnect layer 16 or the metal interconnect layer 22) having the forward tapered side surfaces can be obtained. Although the forward tapered side surfaces of the metal interconnect layer overlap with the gas flow path 30 in plan view of the major surface 10*m* of the substrate 10, steps in the surface on which the gas flow path 30 is formed can be made gentle. Disconnection of the gas flow path 30 and an excessive rise in the film density of the gas flow path 30 are prevented, and the gas flow path 30 having high quality can be stably formed. The sensor 1 in which variation in characteristics is reduced can be obtained.

In the manufacturing method of the sensor 1 of the present embodiment, the metal film (at least one of the metal film 16*p* or the metal film 22*p*) is subjected to dry etching together with part of the first resist layer (at least one of the resist layer 40 or the resist layer 40*b*) with use of an etching gas containing an oxygen gas. A first etching rate of the metal film with respect to the etching gas is higher than a second etching rate of the first resist layer with respect to the etching gas.

Thus, the taper angle (at least one of the taper angle $\theta_2$ or the taper angle $\theta_5$) of the forward tapered side surfaces of the metal interconnect layer (at least one of the metal interconnect layer 16 or the metal interconnect layer 22) can be further decreased. Although the forward tapered side surfaces of the metal interconnect layer overlap with the gas flow path 30 in plan view of the major surface 10m of the substrate 10, steps in the surface on which the gas flow path 30 is formed can be made gentle. The gas flow path 30 having high quality can be stably formed. The sensor 1 in which variation in characteristics is reduced can be obtained.

The manufacturing method of the sensor 1 of the present embodiment further includes forming the insulating layer (at least one of the insulating layer 18 or the insulating layer 24) in which the at least one of the heater 14 or the temperature sensor 20 is filled. The forming the at least one of the heater 14 or the temperature sensor 20 further includes forming the close contact layer (at least one of the close contact layer 17 or the close contact layer 23) that covers the metal interconnect layer (at least one of the metal interconnect layer 16 or the metal interconnect layer 22). The forming the close contact layer includes forming the insulating film (at least one of the insulating film 17p or the insulating film 23p) on the metal interconnect layer and forming the close contact layer having forward tapered outer side surfaces by etching the insulating film. The outer side surfaces of the close contact layer are in contact with the insulating layer. In plan view of the major surface 10m of the substrate 10, the outer side surfaces of the close contact layer overlap with the gas flow path 30.

The close contact layer (at least one of the close contact layer 17 or the close contact layer 23) has the forward tapered outer side surfaces. Thus, although the forward tapered outer side surfaces of the close contact layer overlap with the gas flow path 30 in plan view of the major surface 10m of the substrate 10, steps in the surface on which the gas flow path 30 is formed can be made gentle. Disconnection of the gas flow path 30 and an excessive rise in the film density of the gas flow path 30 are prevented, and the gas flow path 30 having high quality can be stably formed. The sensor 1 in which variation in characteristics is reduced can be obtained. Furthermore, the close contact layer improves close contact between the metal interconnect layer (at least one of the metal interconnect layer 16 or the metal interconnect layer 22) and the insulating layer (at least one of the insulating layer 18 or the insulating layer 24). Separation of the insulating layer from the metal interconnect layer can be prevented. The sensor 1 having stable characteristics can be obtained.

In the manufacturing method of the sensor 1 of the present embodiment, the forming the close contact layer (at least one of the close contact layer 17 or the close contact layer 23) further includes forming a second resist layer (at least one of the resist layer 48 or the resist layer 48b) having forward tapered side surfaces on the insulating film (at least one of the insulating film 17p or the insulating film 23p). The insulating film is etched with use of the second resist layer as a second etching mask.

Thus, the close contact layer (at least one of the close contact layer 17 or the close contact layer 23) having the forward tapered side surfaces can be obtained. Although the forward tapered outer side surfaces of the close contact layer overlap with the gas flow path 30 in plan view of the major surface 10m of the substrate 10, steps in the surface on which the gas flow path 30 is formed can be made gentle. The gas flow path 30 having high quality can be stably formed. The sensor 1 in which variation in characteristics is reduced can be obtained.

In the manufacturing method of the sensor 1 of the present embodiment, the taper angle (at least one of the taper angle $\theta_3$ or the taper angle $\theta_6$) of the outer side surfaces of the close contact layer (at least one of the close contact layer 17 or the close contact layer 23) is equal to or smaller than 45°. Thus, steps in the surface on which the gas flow path 30 is formed can be made gentle. The gas flow path 30 having high quality can be stably formed. The sensor 1 in which variation in characteristics is reduced can be obtained.

In the manufacturing method of the sensor 1 of the present embodiment, the taper angle (at least one of the taper angle $\theta_3$ or the taper angle $\theta_6$) of the outer side surfaces of the close contact layer (at least one of the close contact layer 17 or the close contact layer 23) is equal to or smaller than 20°. Thus, steps in the surface on which the gas flow path 30 is formed can be made gentle. The gas flow path 30 having high quality can be stably formed. The sensor 1 in which variation in characteristics is reduced can be obtained.

In the manufacturing method of the sensor 1 of the present embodiment, the gas flow path 30 is formed of a porous transition metal oxide. Thus, even when the sensor 1 is operated at a high temperature while the sensor part 3 is heated by the heater 14, pores of the gas flow path 30 formed of the porous transition metal oxide hardly aggregate. The sensor 1 in which variation in characteristics is reduced can be obtained.

In the manufacturing method of the sensor 1 of the present embodiment, the gas flow path 30 is formed by an oblique evaporation method.

Because steps in the surface on which the gas flow path 30 is formed can be made gentle, the lowering of the evaporation angle when an evaporated material for forming the gas flow path 30 is obliquely evaporated onto the surface on which the gas flow path 30 is formed is small. Thus, disconnection of the gas flow path 30 and an excessive rise in the film density of the gas flow path 30 are prevented, and the gas flow path 30 having high quality can be stably formed. The sensor 1 in which variation in characteristics is reduced can be obtained. In the present specification, the evaporation angle is defined as the angle between the normal direction of the surface on which the gas flow path 30 is formed and the evaporation direction of the evaporated material.

In the manufacturing method of the sensor 1 of the present embodiment, forming the sensor part 3 includes forming the gas flow path 30, forming the porous electrode (first porous electrode 31) on the gas flow path 30, and forming the solid electrolyte layer 32 in contact with the porous electrode. Thus, the sensor 1 that is a limiting current-type gas sensor in which variation in characteristics is reduced can be obtained.

It should be considered that the embodiment and the modification examples thereof disclosed this time are exemplification in all respects and are not what are restrictive. It is intended that the range of the present disclosure is described by not the above explanation but the scope of claims and all changes within meanings and range equivalent to the scope of claims are included therein.

What is claimed is:
1. A sensor, comprising:
a substrate that includes a major surface;
a first nitride layer;
a second nitride layer;
a first insulating layer;

a sensor part that includes:
a gas flow path formed of a porous material, wherein a film density of the gas flow path is equal to or lower than 80%, and
a first porous electrode formed on the gas flow path; and
at least one of a heater or a temperature sensor, wherein
the heater is configured to heat the sensor part,
the temperature sensor is configured to measure temperature of the sensor part,
the sensor part and the at least one of the heater or the temperature sensor are stacked over the major surface,
the second nitride layer is on the first nitride layer,
the temperature sensor is on the first nitride layer,
the temperature sensor is embedded in the second nitride layer,
the heater is embedded in the first insulating layer,
the first nitride layer is between the first insulating layer and the second nitride layer,
the first nitride layer is different from the first insulating layer,
the gas flow path is between the second nitride layer and the first porous electrode,
the at least one of the heater or the temperature sensor is an interconnect having forward tapered side surfaces,
the at least one of the heater or the temperature sensor includes a metal interconnect layer, and
the forward tapered side surfaces of the interconnect overlap with the gas flow path in plan view of the major surface.

2. The sensor according to claim 1, wherein a taper angle of the forward tapered side surfaces of the interconnect is equal to or smaller than 45°.

3. The sensor according to claim 1, wherein a taper angle of the forward tapered side surfaces of the interconnect is equal to or smaller than 20°.

4. The sensor according to claim 1, wherein
the metal interconnect layer has forward tapered side surfaces, and
the forward tapered side surfaces of the metal interconnect layer overlap with the gas flow path in the plan view of the major surface.

5. The sensor according to claim 4, wherein a taper angle of the forward tapered side surfaces of the metal interconnect layer is equal to or smaller than 45°.

6. The sensor according to claim 4, wherein a taper angle of the forward tapered side surfaces of the metal interconnect layer is equal to or smaller than 20°.

7. The sensor according to claim 1, wherein the metal interconnect layer is formed of platinum.

8. The sensor according to claim 1, wherein
the heater further includes a close contact layer that covers the metal interconnect layer,
the close contact layer has forward tapered outer side surfaces in contact with the first insulating layer, and
the forward tapered outer side surfaces of the close contact layer overlap with the gas flow path in the plan view of the major surface.

9. The sensor according to claim 8, wherein a taper angle of the forward tapered outer side surfaces of the close contact layer is equal to or smaller than 45°.

10. The sensor according to claim 8, wherein a taper angle of the forward tapered outer side surfaces of the close contact layer is equal to or smaller than 20°.

11. The sensor according to claim 8, wherein the close contact layer is formed of one of titanium oxide, chromium oxide, tungsten oxide, molybdenum oxide, or tantalum oxide.

12. The sensor according to claim 1, wherein the gas flow path is formed of a porous transition metal oxide.

13. The sensor according to claim 1, wherein
the sensor part further includes:
a solid electrolyte layer in contact with the first porous electrode, and
the forward tapered side surfaces of the interconnect overlap with the solid electrolyte layer in the plan view of the major surface.

14. The sensor according to claim 13, wherein the sensor part further includes:
a second porous electrode on the first porous electrode and the solid electrolyte layer, and
a second insulating layer between the solid electrolyte layer and the second porous electrode.

* * * * *